United States Patent
Zhu et al.

(10) Patent No.: US 9,645,156 B2
(45) Date of Patent: May 9, 2017

(54) METHOD FOR DETERMINING GLYCOSYLATION AND TERMINAL MODIFICATION OF SAMPLES DURING PROTEIN PURIFICATION PROCESS

(71) Applicant: LIVZON MABPHARM INC., Zhuhai, Guangdong (CN)

(72) Inventors: Baoguo Zhu, Guangdong (CN); Yucai Peng, Guangdong (CN); Jiaming Yang, Guangdong (CN)

(73) Assignee: LIVZON MABPHARM INC., Zhuhai, Guangdong Province (CN)

( * ) Notice: Subject to any disclaimer, the term of this patent is extended or adjusted under 35 U.S.C. 154(b) by 0 days.

(21) Appl. No.: 14/760,313

(22) PCT Filed: Apr. 24, 2013

(86) PCT No.: PCT/CN2013/074596
§ 371 (c)(1),
(2) Date: Jul. 10, 2015

(87) PCT Pub. No.: WO2014/110874
PCT Pub. Date: Jul. 24, 2014

(65) Prior Publication Data
US 2015/0362506 A1 Dec. 17, 2015

(30) Foreign Application Priority Data
Jan. 15, 2013 (CN) .......................... 2013 1 0027640

(51) Int. Cl.
*G01N 33/68* (2006.01)
*G01N 30/06* (2006.01)
*G01N 30/72* (2006.01)
G01N 30/88 (2006.01)
G01N 30/02 (2006.01)

(52) U.S. Cl.
CPC ......... *G01N 33/6848* (2013.01); *G01N 30/06* (2013.01); *G01N 30/7233* (2013.01); *G01N 33/6854* (2013.01); G01N 2030/027 (2013.01); G01N 2030/065 (2013.01); G01N 2030/067 (2013.01); G01N 2030/8831 (2013.01); G01N 2440/38 (2013.01); G01N 2560/00 (2013.01); Y10T 436/24 (2015.01)

(58) Field of Classification Search
CPC .... G01N 30/02; G01N 30/72; G01N 30/7233; G01N 30/06; G01N 33/68; G01N 33/6848; G01N 33/6854; G01N 33/6857; G01N 2030/027; G01N 2030/065; G01N 2030/067; G01N 2030/8831; G01N 2440/38; G01N 2560/00; Y10T 436/24; Y10T 436/25375; H01J 49/00; H01J 49/26
USPC ... 436/86, 87, 161, 173, 174, 177, 513, 547, 436/548; 422/430
See application file for complete search history.

(56) References Cited

U.S. PATENT DOCUMENTS

| | | | |
|---|---|---|---|
| 2005/0161399 A1 | 7/2005 | Dillon et al. | |
| 2008/0299678 A1 | 12/2008 | Wu et al. | |
| 2009/0069549 A1* | 3/2009 | Georges | C07K 1/145 530/412 |
| 2011/0294150 A1* | 12/2011 | Koll | C07K 1/20 435/23 |
| 2012/0172255 A1* | 7/2012 | Haberger | G01N 33/50 506/12 |

FOREIGN PATENT DOCUMENTS

| | | |
|---|---|---|
| CN | 101177453 A | 5/2008 |
| CN | 102308216 A | 1/2012 |
| CN | 102675460 A | 9/2012 |
| WO | 2009/065414 A1 | 5/2009 |
| WO | 2010/141249 A2 | 12/2010 |
| WO | 2011/026640 A1 | 3/2011 |

OTHER PUBLICATIONS

Chevreux et al. Analytical Biochemistry, vol. 415, Apr. 27, 2011, pp. 212-214.*
Johnson et al. Analytical Biochemistry, vol. 360, 2007, pp. 75-83.*
Yang et al. Analytical Biochemistry, vol. 448, Nov. 25, 2013, pp. 82-91.*
Yin et al. Pharm. Res., vol. 30, Sep. 6, 2012, pp. 167-178.*
Cai, Yun, et al; "Application of mass spectrometry in analysis of glycoprotein", Letters in Biotechnology, vol. 13, No. 5. Sep. 2002; 4 pages.
International Search Report mailed Oct. 24, 2013; PCT/CN2013/074596.
Joan Christie Han, et al; "A Procedure for Quantitative Determination of Tris(2-carboxyethyl)phosphine, an Odorless Reducing Agent More Stable and Effective Than Dithiothreitol", Analytical Biochemistry, vol. 220, pp. 5-10, Jul. 1994.

(Continued)

*Primary Examiner* — Maureen Wallenhorst
(74) *Attorney, Agent, or Firm* — Ladas & Parry LLP

(57) ABSTRACT

The present invention provides a method for determining glycosylation and terminal modifications of immunoglobulin during immunoglobulin purification process, which can simultaneously and rapidly determine glycosylation, N-terminal pyroglutamination and C-terminal de-lysination of immunoglobulin, including Step 1) separating immunoglobulin by using cation-exchange resin, and collecting different components in according to retention time; Step 2) denaturing the components of immunoglobulin obtained in step 1) with a denaturant, followed by reducing them with a reducing agent, to separate the light chain and heavy chain; Step 3) separating the light chain and heavy chain of immunoglobulin of step 2) by using reverse phase ultrahigh pressure liquid chromatography; Step 4) measuring the molecular weights of the light chain and heavy chain obtained in step 3) with mass spectrum; and Step 5) analyzing the chromatographic data obtained in step 3) and the mass spectrometric data obtained in step 4) to determine glycosylation and terminal modifications of the immunoglobulin.

12 Claims, 21 Drawing Sheets

(56) References Cited

OTHER PUBLICATIONS

Zhi-Guang Liu, et al; "One-step purification of McAb preparation scale using cation exchange liquid chromatography", Journal of The Fourth Military Medical University; vol. 15(4); pp. 293-296; Apr. 1994.

Douglas S. Rehder, et al; "Reversed-phase liquid chromatography/mass spectrometry analysis of reduced monoclonal antibodies in pharmaceutics", Journal of Chromatography A. 1102; pp. 164-175; Available online Nov. 17, 2005.

Henry Shion, et al; "Structural characterization of therapeutic monoclonal antibody Trastuzumab by LC/MS and LC/MS$^E$", Chinese Journal of New Drugs 23(4): pp. 418-426+431; Feb. 2014.

Nicole Stackhouse, et al; "A High-Throughput UPLC Method for the Characterization of Chemical Modifications in Monoclonal Antibody Molecules", Journal of Pharmaceutical Sciences, vol. 100, No. 12, Dec. 2011; pp. 5115-5125.

Yangjun Zhang, et al; "Advances of separation and analytical techniques in proteam ic studies", Chinese Journal of Chromatography, Sep. 2009; vol. 27, No. 5, pp. 537-550.

Supplementary European Search Report completed Jun. 22, 2016; EP 13 87 1613.

* cited by examiner

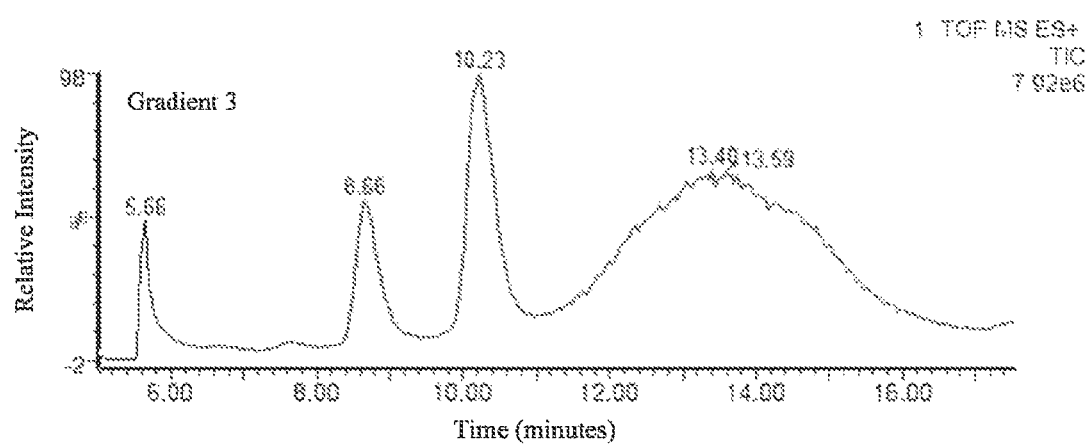
Figure 3C
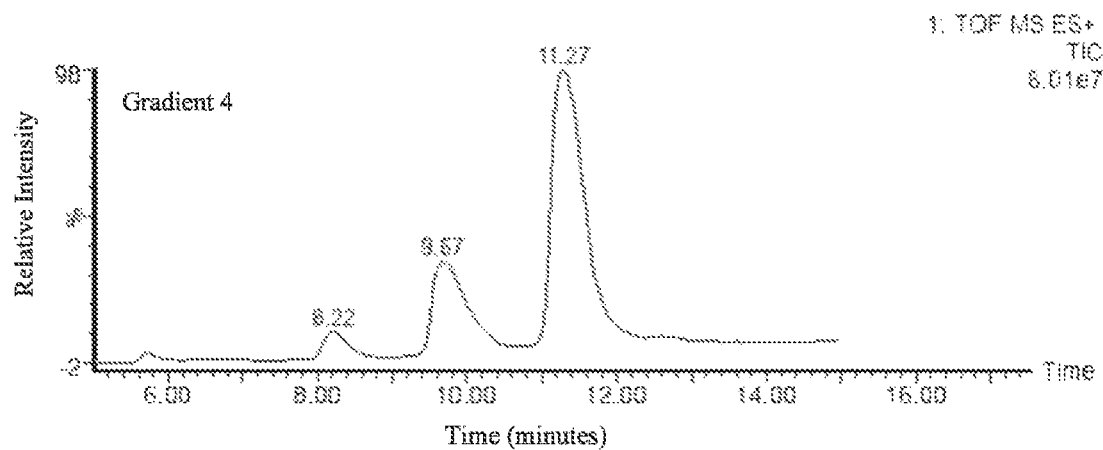
Figur 3D

METHOD FOR DETERMINING GLYCOSYLATION AND TERMINAL MODIFICATION OF SAMPLES DURING PROTEIN PURIFICATION PROCESS

TECHNICAL FIELD

The present invention relates to biotechnology field. Specifically, the present invention provides a method for determining glycosylation and terminal modifications of samples during protein purification process. Meanwhile, the present invention also relates to a kit for determining protein glycosylation and terminal modification during immunoglobulin purification process.

BACKGROUND

Over the past decade, monoclonal antibodies achieved significant success and tremendous growth in bio-pharmaceutical industry, as well as the entire pharmaceutical industry. Compared with the traditional small molecule drugs, monoclonal antibodies possess many advantages including good specificity, significant therapeutic effect, less side effects, small administration amount, and so on. Regarding the characteristics of drug molecule, the antibodies have greater heterogeneity. This property of the antibodies is caused by a variety of factors, of which post-translational modification is the most important internal factor. Common post-translational modifications include antibody glycosylation, N terminal pyroglutamination, C terminal delysination, deamidizatioin, oxidation, isomerization and the like. Post-translational modifications will be detected and analyzed in many steps during antibody drug development, such as molecular identification, process development, quality control, etc.

IgG antibody glycosylation occurs at asparagine in heavy chain Fc region, which belongs to N-glycosylation, and an important structural components of the antibody. The core unit of IgG sugar chain is formed by connecting bifurcating structures formed by two N-acetylglucoses and three mannitoses. According to the differences in terminal galactose, core fucose, terminal sialic acid or the like, a variety of sugar chain structures can be constructed. IgG glycosylation is uneven because of different glycoform and content. The differences in glycosylation may affect the biological activity and pharmacokinetic characteristics of the antibody, such as CDC, ADCC, in vivo elimination half-life and the like.

When the N-terminal amino acid of the IgG antibody is glutamine, cyclization occurs readily to produce pyroglutamic acid, pyroE. The reaction can be spontaneous, or may be conducted under enzyme catalysis conditions. At C terminus of the IgG antibody molecule, de-lysine (—K) reaction occur readily. In most cases, both have no effect on biological activity of the antibody, but it is also reported that the N-terminal pyroglutamination of some antibodies may affect their antigen binding force. In addition, N terminal pyroglutamination and C terminal de-lysination will affect the charge distribution of the antibody, and charge characteristic is one of the important indicators of antibody quality control.

Therefore, it has important significance to establish an analysis method for rapid determination of IgG antibody glycosylation and terminal modification in the development of antibodies. Currently in the art, glycosylation and terminal modification are generally determined separately. Enzymatic quantitative fluorescence labeling method is a classic quantitative assay for determining IgG1 glycosylation, but the sample handling is quite complicated and time-consuming, and requires a large amount of sample. Mass spectrometry is also used for glycosylation analysis by detecting IgG enzymolysis fragments, such as papain enzyme and IdeS enzyme. However, these methods have some disadvantages, such as weak enzyme cleavage site selectivity, or high cost, or complicated sample handling, and hence they are inappropriate for batch testing of conventional or process development samples. Application of LC-MS in peptide mapping analysis is theoretically possible to determine the glycosylation and terminal modification of antibody at the same time, but there are many technical difficulties in the separation, determination and data analysis of sugar-containing polypeptides. Thus, it is inappropriate for quantitative analysis of glycosylation, and the sample handling is quite complicated and time-consuming, the digestion process may also have an impact on the existing terminal modification of antibodies. In immunoglobulin purification process, it is required to determine the protein purification status at any time, thus the large amount of sample required for detection and long detection time are still the biggest problems. Therefore, a suitable method for simultaneously and rapidly determining the glycosylation and terminal modifications of a small amount of IgG antibody during antibody development has not been reported yet.

SUMMARY OF THE INVENTION

To solve the above problems, an object of the invention is to provide a method for simultaneous determination of sample glycosylation and terminal modification during the purification process of immunoglobulin (i.e., antibody). The invention also relates to a kit for determining protein glycosylation and terminal modification during immunoglobulin purification process.

The present invention provides a method for simultaneous determination of sample glycosylation and terminal modifications during the purification process of immunoglobulin, comprising the following steps of:
1) Separating immunoglobulin by using cation-exchange chromatography, and collecting different components according to retention time;
2) Denaturing the immunoglobulin components obtained in step 1) with a denaturant, followed by reducing with a reducing agent, to separate the light chain and heavy chain;
3) Separating the light chain and the heavy chain of immunoglobulin of step 2) by using reverse phase ultrahigh pressure liquid chromatography;
4) Measuring molecular weights of the light chain and the heavy chain obtained in step 3) with mass spectrum;
5) Analyzing the chromatographic data obtained in step 3) and the mass spectrometric data obtained in step 4) to determine glycosylation and terminal modifications of said immunoglobulin.

Wherein the immunoglobulin is preferably human immunoglobulin, preferably human immunoglobulin IgG, and more preferably human IgG1 and IgG2 immunoglobulin subtypes.

Further, the glycosylation and terminal modifications of the immunoglobulin preferably include N-terminal pyroglutamination of light chain, and asparagine glycosylation, N-terminal pyroglutamination, and C-terminal de-lysination of heavy chain of the immunoglobulin.

In the method of the present invention, said step 1) comprises:
Using conventional strong cation-exchange chromatography column with 20 mM sodium phosphate buffer as loading buffer, 20 mM sodium phosphate and 1 M sodium chloride buffer (pH=6.0) as elution buffer, and monitoring the eluting components by UV absorption at 280 nm.

Specifically, said step 2) comprises: adding about 10-30 μL of 1-6 M guanidine hydrochloride aqueous solution to a certain amount of immunoglobulin, after homogenously mixing, adding 1-4 μL dithiothreitol (DTT) aqueous solution to denature and reduce the immunoglobulin, wherein the final concentration of DTT in the reaction solution is 25-100 mM, and the final concentration of immunoglobulin is 0.2-3 μg/μL.

Preferably, in said step 2), the final DTT concentration is 50 mM.

Preferably, in said step 2), the temperature for immunoglobulin denaturation and reduction is 50-65° C., and the reaction time is 45 min-120 min.

More preferably, in said step 2), the temperature for immunoglobulin denaturation and reduction is 65° C., and the reaction time is 45 min.

Specifically, said step 3) comprises:

Separating the light chain and heavy chain of immunoglobulin of step 2) with reverse phase ultrahigh pressure liquid chromatography to achieve a baseline separation of the light and the heavy chains. According to specific embodiments of the present invention, the liquid system can be UPLC (Waters, ACQUITY). Chromatography Column: Waters, ACQUITY UPLC column, BEH C4, 1.7 μm (size), 300 Å (diameter), 2.1×50 mm.

The elution conditions for the mobile phase greatly affect the separation of the light and heavy chains, and preferably the chromatographic conditions are set as follows:

Column temperature is set at 55-65° C., with a injection amount of 0.2-3 μg;

The mobile phase X is 0.1% formic acid in water, phase Y is 0.1% formic acid in acetonitrile, with a flow rate of 0.4 mL/min;

Gradient elution conditions:

| Time (min) | Mobile phase X | Mobile Phase Y | Flow rate (mL/min) |
|---|---|---|---|
| 0 | 90 | 10 | 0.4 |
| 5 | 90 | 10 | 0.4 |
| 5.1 | 75 | 25 | 0.4 |
| 15 | 65 | 35 | 0.4 |
| 15.1 | 10 | 90 | 0.4 |
| 18 | 10 | 90 | 0.4 |
| 18.1 | 90 | 10 | 0.4 |
| 21 | 90 | 10 | 0.4 |

Specifically, said step 4) comprises:

Determining the molecular weights of the light and heavy chains obtained in step 3) using electrospray ionization mass spectrometry, wherein at 0-5 min, the flow path leads to waste, and at 5-16 min, the flow path leads to MS, then collecting mass spectrometric data in positive ion mode;

Preferably, the MS conditions are set as follows:

Cone gas flow is about 50.0 L/Hr, desolvation gas is about 500-800.0 L/Hr, desolvation temperature is about 350-500° C., scan range is about 400-2500 Da, and the scan time is about 0.5-2 s. Sampling cone voltage greatly affects the MS signal, and is set to about 20-40V, preferably set to 20-30V.

Specifically, said step 5) comprises:

Calculating the ratio of N-terminal pyroglutamination of light chain of immunoglobulin from the chromatographic peak area obtained in step 3), and calculating with deconvolution the relative contents of glycoforms, and the ratios of N-terminal pyroglutamination and C-terminal de-lysination of heavy chain of immunoglobulin from the MS data obtained in step 4).

Specifically, the method is applied to a kit for determining protein glycosylation and terminal modification in immunoglobulin purification.

In the reduction reaction of immunoglobulin, protein disulfide linkages are broken under the effect of DTT, generating two identical light chains and two identical heavy chains. C4 reverse-phase ultrahigh pressure liquid chromatography is used to separate the mixture of light and heavy chains, and the light and heavy chains with or without N-terminal pyroglutamic acid (containing different glycoforms and terminal modifications) can achieve a baseline separation. Then ESI-MS is used to online determine their molecular weights. Since the heavy chains with different glycoforms and/or terminal modifications have different molecular weights, and the ratios of each kind of heavy chains are directly proportional to their molecular weight peak intensities, the relative contents of glycoforms, and the ratios of N-terminal pyroglutamination and C-terminal de-lysination of the heavy chains can be obtained by calculating the MS data for the heavy chains. Furthermore, the proportion of N-terminal pyroglutamination of the light chains can be obtained by calculating the chromatographic peak area.

Currently there are several techniques in the art to determine the molecular weights of a protein or its modification. However, compared with the method of the present invention, these methods all have defects or deficiencies. For example, mass spectrometry (MS), such as MALDI-MS, is usually used to determine the molecular weight of antibody whole protein. Even though mass spectrometry has good compatibility with samples and is easy to operate, but the results of measured molecular weight have lower resolution. As a classical quantitative method for IgG antibody glycosylation, Enzymatic quantitative fluorescence labeling method uses N-glycosidase, PNGaseF to enzymatically digest IgG to obtain sugar chain, which is purified, fluorescence labeled, and subjected to a high performance liquid chromatography or capillary electrophoresis analysis. This method is highly selective with high accuracy, but the sample preparation process is complex, and time-consuming (usually taking two days), and requires a large amount of sample (generally at least 100 μg). ESI-MS is also used to measure IgG enzymolysis fragments for glycosylation analysis, but the selectivity of papain enzyme cleavage site is low, resulting in increased byproducts to affect data analysis. Immunoglobulin G degrading enzyme S (IdeS) is highly selective, but costly, thus inappropriate for normal or process development routine batch testing of samples. Application of LC-MS analysis in pancreatin peptide mapping is theoretically possible to determine the glycosylation and terminal modification of antibody at the same time, but there are many technical difficulties in the separation, determination and data analysis of sugar-containing polypeptides, and its detection sensitivity is low, thus it is inappropriate for determination of low content glycosyl. Besides, the sample handling is quite complicated and time-consuming, and the digestion process may also have an impact on the existing terminal modification of antibodies.

In contrast, the method of the present invention uses ESI-MS to measure antibody multiply-charged ions, and then perform deconvolution calculation, thus greatly improving the resolution and accuracy of the test results (<30 ppm). In addition, the present invention is characterized in simple sample handling, requiring only a reducing agent to conduct reaction (45 min), small amount of sample (5 μg), and UPLC-MS detection of samples just completed within 16 min, meanwhile the data for antibody glycosylation, N-terminal pyroglutamination and C-terminal de-lysination can be obtained. The present invention is particularly applicable to experiments with a small amount of test sample, such as clones screening, and rapid batch detection during process development. Meanwhile, the present invention is also applicable to sample detection in conventional dosage (100 μg). The method of the present invention can detect glycosylation and terminal modification of different antibodies, such as IgG1, and IgG2, and also can be used to test the sample in antibody process development. Furthermore, in combination with carboxypeptidase B and cation-exchange chromatography (CEX-HPLC), the method of the present invention can also be applied to characterize and identify the structures of antibody charge isomers.

Immuneglobulin can be divided into five categories, IgG, IgA, IgM, IgD, and IgE, wherein IgG can be divided IgG1, IgG2, IgG3, IgG4 and other subtypes. Currently on market, 70%-80% monoclonal antibody drugs are IgG1-like proteins. According to the composition of human amino acid sequences in IgG1 antibody, it can be classified as chimeric antibody IgG1, humanized IgG1 antibodies, and other proteins. The present invention provides a method for determining glycosylation and terminal modification of samples during immunoglobulin purification process, especially, a method for determining glycosylation and terminal modification of Immunoglobulins IgG1 and IgG2. The method of the present invention can simultaneously and rapidly determine glycosylation, N-terminal pyroglutamination and C-terminal de-lysination of immunoglobulin during protein purification. Specifically, the present invention reduces a small amount of protein during protein purification, and separates the light chain and heavy chain properly, without affecting original glycosylation and terminal modification conditions of the immunoglobulin. The reduced human immunoglobulin (i.e., antibody) is analyzed by using high pressure liquid chromatography coupled with mass spectrometry, capable of simultaneously and rapidly determining glycosylation, N-terminal pyroglutamic acid cyclization and C-terminal de-lysination of a small amount of immunoglobulin (especially human immunoglobulin).

BRIEF DESCRIPTION OF DRAWINGS

Hereinafter, the embodiments of the present inventions are described in details with reference to drawings, wherein:

FIGS. 3A-3D show the comparisons of the effect of eluting gradients 1, 2, 3, and 4 on the separation of the light and heavy chains in Example 1.

FIG. 5B-1 to FIG. 5B-3 show chromatograms of light chain, pyroglutaminated light chain and heavy chain of antibody A determined after reduction. FIGS. 5D-1 to 5D-2 show chromatograms of light chain and heavy chain of antibody B determined after reduction. pyroE is N-terminal pyroglutamic acid, —K means C-terminal de-lysine, and —H$_2$O means dehydrated.

FIGS. 6A-1 and 6A-2 show chromatograms of cation-exchange resin component 1 and component 5 of antibody A determined after reduction in Example 3; FIGS. 6B-1 and 6B-2 show mass spectra of the heavy chains of component 1 and component 5 of antibody A determined after reduction. pyroE is N-terminal pyroglutamic acid, —K means C-terminal de-lysine, and —H2O means dehydrated.

DETAILED EMBODIMENTS

Figure 1A:
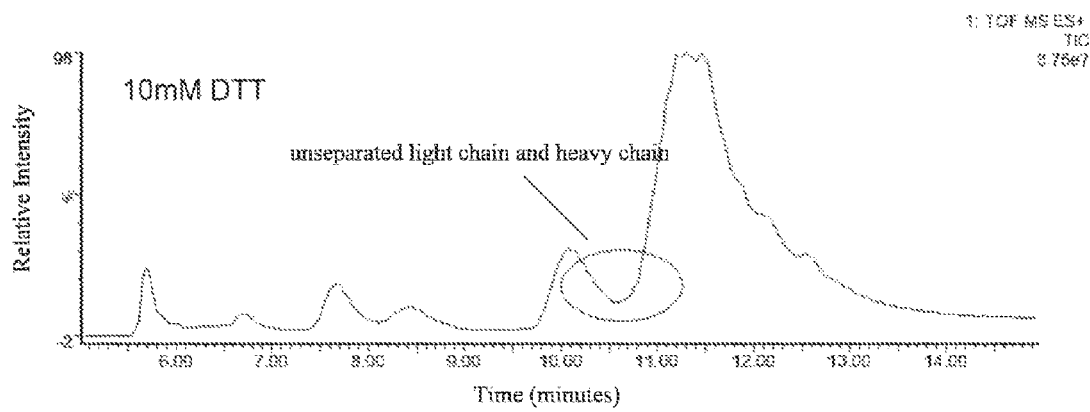
FIGS. 1A-1D show the comparison results of different amounts of DTT to separate the light and heavy chains of antibody A in Example 1.
Figure 1B:
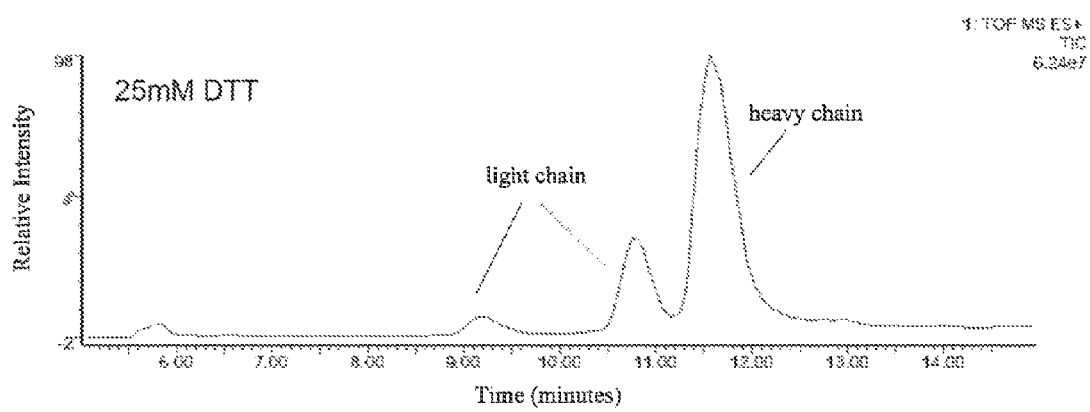
Figure 1C:
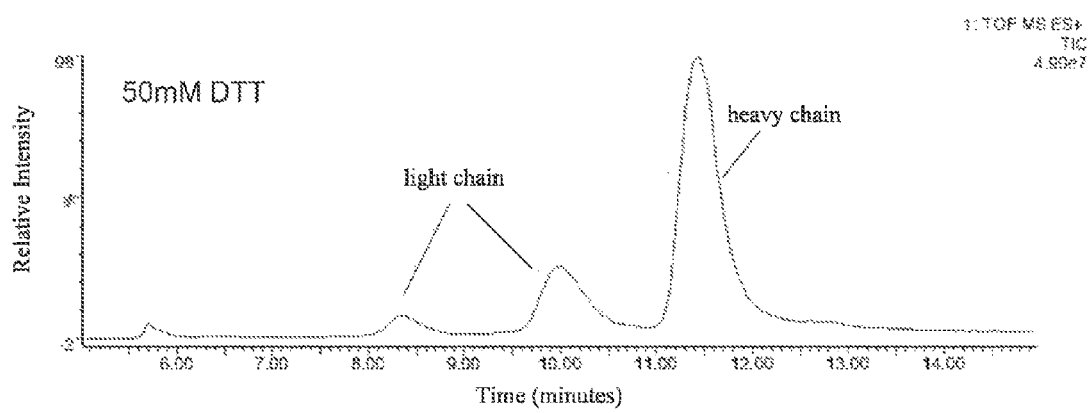
Figure 1D:
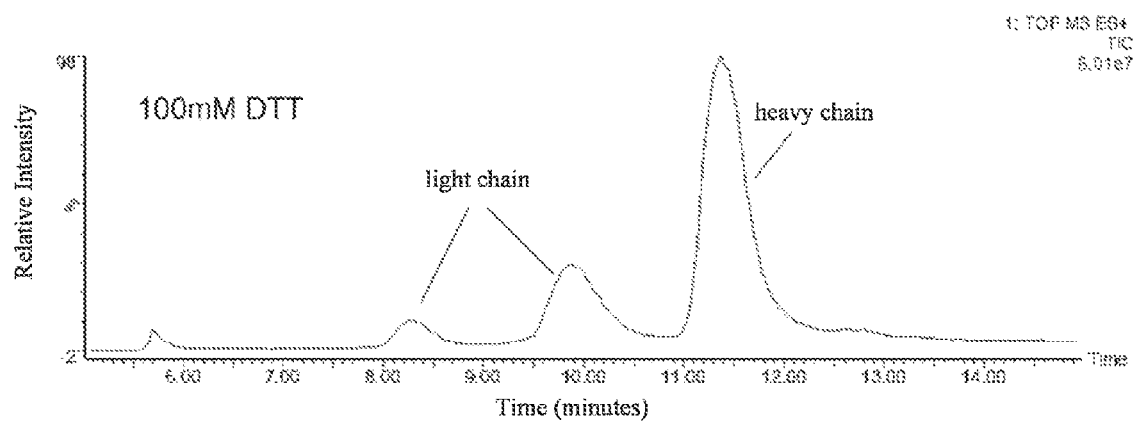

With reference to specific embodiments, the present invention will be described. The skilled persons in the art will understand that these embodiments are intended to illustrate the invention, without in any way limiting the scope of the present invention.

In the following examples, antibody A is a chimeric antibody IgG1 (the specific preparations are described in Chinese patent: CN101177453B, specification pages 10-13, Examples 1-6, wherein the C2-11-12 chimeric antibody screened out in Example 6 on page 13 of the specification is the antibody A of the present invention); antibody B is a humanized antibody IgG1, (manufactured by Zhuhai Lizhu Mab Biotechnology Co., Ltd., the specific preparations are described in Chinese patent: CN102675460A, specification pages 12-18, Examples 1-7, wherein the AT-132 antibody screened out in Example 6 on pages 17-18 of the specification is the antibody B of the present invention); antibody C is a full length humanized IgG2, manufactured by Amgen Canada Inc.

The experimental methods described in examples below, unless otherwise noted, are conventional methods. Medicinal materials and reagent materials used in the following examples, unless otherwise noted, are commercially available products.

EXAMPLE 1

Determination of Conditions for Immunoglobulin Reducing Method 1.1 Determination of the Amount of Reducing Agent DTT The effects of four different amounts of DTT on separation of the light and heavy chains were examined. 4 aliquots of 5 μg antibody protein A were respectively added to 10 μL 6 M guanidine hydrochloride solution, followed by the addition of 0.1 M DTT solution, 2 μL and 5 μL, and 0.5 M DTT solution, 2 μL and 4 μL, as well as appropriate amounts of 6 M guanidine hydrochloride solutions to make final DTT concentrations of 10 mM, 25 mM, 50 mM, and 100 mM, respectively. Then the resulting products were reacted with said IgG1 protein at 65° C. for 45 min.

C4 reverse-phase high pressure liquid chromatography was used to separate the light and heavy chains obtained in the reactions, and the liquid phase system used was UPLC (Waters, ACQUITY). Column: Waters, ACQUITYUPLC column, BEH C4, 1.7 μm (diameter), 300 Å (aperture), 2.1×50 mm. Chromatographic conditions were set as follows: the column temperature was set to 60° C., injection volume was 1 μg; mobile phase X was 0.1% formic acid in water, mobile phase Y was 0.1% formic acid in acetonitrile and flow rate was 0.4 mL/min; gradient elution conditions were:

| Time (min) | Mobile phase X | Mobile Phase Y | Flow rate (mL/min) |
|---|---|---|---|
| 0 | 90 | 10 | 0.4 |
| 5 | 90 | 10 | 0.4 |
| 5.1 | 75 | 25 | 0.4 |
| 15 | 65 | 35 | 0.4 |
| 15.1 | 10 | 90 | 0.4 |
| 18 | 10 | 90 | 0.4 |
| 18.1 | 90 | 10 | 0.4 |
| 21 | 90 | 10 | 0.4 |

Electrospray ionization mass spectrometry was used to determine the molecular weights of the light and the heavy chains separated by chromatography, wherein at 0-5 min, the flow path led to waste, at 5-16 min, the flow path led to MS, then mass spectrometry data were collected in a positive ion mode. The MS conditions were set as follows: cone gas flow was 50.0 L/Hr, desolvation gas was 800.0 L/Hr, desolvation temperature was 500° C., scan range was 400-2500 Da, scan time was 1 s, and sampling cone voltage was set to 25V.

The results were shown in FIGS. 1A-1D. When the DTT final concentration was 10 mM, antibody A light chain and heavy chain were not completely separated. When the DTT concentration was 25 M, the light chain and heavy chain were completely separated in most cases, but in very few samples the chromatographic separation was not ideal. When the DTT concentration was 50-100 mM, the light and heavy chains in all antibody samples were completely separated. To ensure the antibody light and heavy chains separation and chromatographic separation, it was ascertained that 25-100 mM DTT was used as an appropriate amount of reducing agent for 0.2-3 μg/μL antibody protein, preferably 50 mM.

1.2 Determination of Reduction Reaction Temperature and Time

Several aliquots of 5 μg antibody A were added to 10 μL 6 M guanidine hydrochloride solution, followed by the addition of 0.5 M DTT solution 2 μL and then an appropriate amount of 6 M guanidine hydrochloride solution, to make a final DTT concentration of 50 mM. Three reaction temperatures 37° C., 50° C., and 65° C. and reaction time between 20 min to 120 min were investigated for their effects on the light chain and heavy chain separation, and terminal modification of antibody IgG. Chromatography and mass spectrometry conditions were the same as described in Example 1.1.

Experimental data were processed with Waters BiopharmaLynx 1.3 software. An "Intact Protein" mode was selected for performing deconvolution process, and the method parameters were as follows: Lock Mass (Da): 556.2771; TIC Threshold: 300-500: Deconvolution m/z Range: light chain 850-2000, heavy chain 950-1500; Protein MW Range: light chain 20000-30000 Da, heavy chain 42000-60000 Da. The proportions of each IgG antibody glycoform were obtained by normalizing the intensity of molecular weight peak of each glycoform in heavy chain mass spectrum. N-terminal pyroglutamic acid containing light chains and N-terminal pyroglutamic acid free light chains can achieve a baseline separation. Therefore, the proportion of light chain N-terminal pyroglutamination can be calculated from integrating the peak areas. The heavy chain N-pyroglutamination and de-lysination can be obtained by analyzing molecular weight of G0F heavy chain.

Figures 1, 2A:
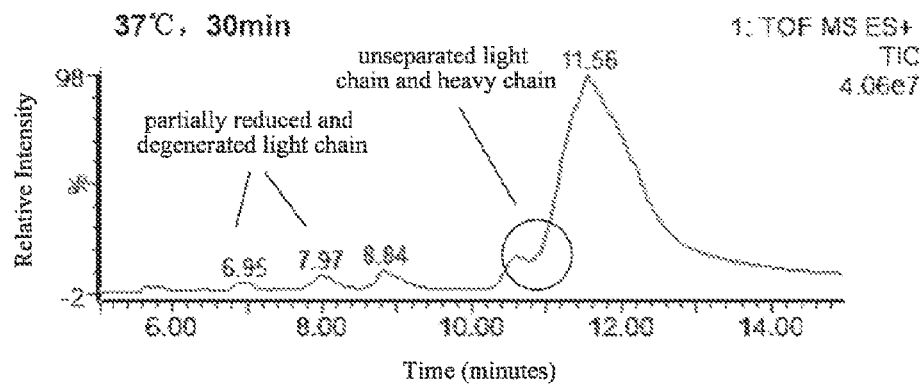
FIGS. 2A-1, 2A-2, 2A-3, 2B-1, 2B-2, 2B-3, 2C-1, 2C-2, and 2C-3 show the effects of different DTT reduction reaction temperatures and time on the separation of the light and heavy chains and the terminal modifications in Example 1.
Figures 2, 2A:
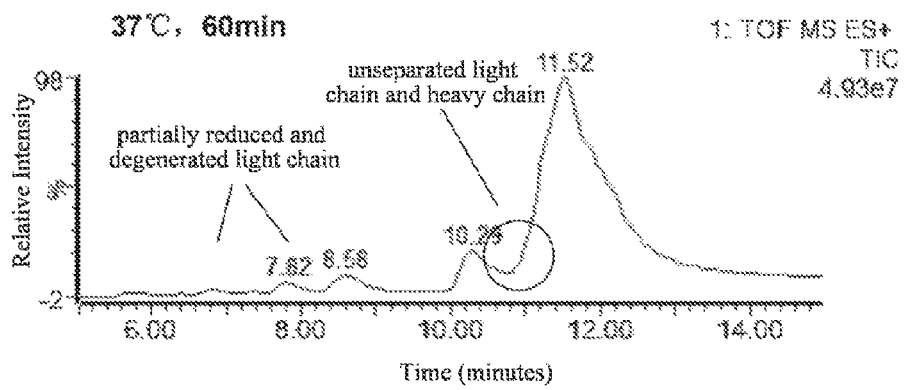

Specific results were shown in FIG. 2 and Table 1. As seen from FIG. 2A-1 to FIG. 2A-3, when the reduction temperature was 37° C., the antibody light and heavy chains were not completely separated, indicating that at this temperature, the reduction reaction was not complete. As seen from FIGS. 2B-1 to 2B-3, and 2C-1 to 2C-3, when the reduction temperature was 50° C. and 65° C. (reaction time≥45 min), the separation of the antibody light and heavy chains were ideal, indicating that DTT reduction were almost completely at a temperatures above 50° C. In addition, as can be seen in Table 1, at the same temperature, the longer the reaction time, the higher the proportions of terminal modifications of light and heavy chains. Similarly, in the same reaction time, the higher the reaction temperature, the higher the proportions of terminal modifications of light and heavy chains. And, taking into account that high temperature conditions were likely to promote N-terminal pyroglutamination and C-terminal de-lysination reactions, the effect of sample preparation on terminal modification should be investigated. As shown in Table 1, when the reaction time was between 45 min and 120 min, the variation in terminal modification was not significant. Therefore, the preparation conditions adopted had little influence on antibody terminal modification.

TABLE 1

Comparison of antibody IgG1 terminal modifications under different DTT reduction temperature and time conditions

| DTT Reduction Conditions | | Modification proportion | | |
|---|---|---|---|---|
| Temperature | Time (min) | Pyroglutamination (light chain) | Pyroglutamination (heavy chain) | Delysination (heavy chain) |
| 37° C. | 30 | — | 81.22 | 85.42 |
| | 45 | 70.47 | 80.59 | 85.04 |
| | 60 | 70.55 | 81.68 | 84.32 |
| | 90 | 75.53 | 81.89 | 85.12 |
| | 120 | 77.66 | 80.33 | 86.71 |
| 50° C. | 30 | 71.38 | 81.87 | 84.39 |
| | 45 | 77.13 | 83.10 | 86.60 |
| | 60 | 78.75 | 82.31 | 87.13 |
| | 90 | 80.62 | 81.39 | 87.45 |
| | 120 | 80.67 | 79.78 | 88.45 |
| 65° C. | 30 | 80.56 | 81.20 | 87.17 |
| | 45 | 81.12 | 82.62 | 87.41 |
| | 60 | 81.11 | 82.13 | 88.45 |
| | 90 | 81.58 | 81.81 | 88.05 |
| | 120 | 81.12 | 81.24 | 89.30 |

In summary, the reduction reaction conditions were determined as: reacting at 50-65° C., reaction time between 45 min and 120 min.

1.3 Accuracy and Reproducibility of the Method

Under the optimized experimental conditions (Several aliquots of 5 μg antibody A were added to 10 μL 6 M guanidine hydrochloride solution, followed by the addition of 0.5M DTT solution 2 μL and an appropriate amount of 6 M guanidine hydrochloride, to make a final DTT concentration of 50 mM; reacting for 45 min at 65° C.), the accuracy and reproducibility of the method of the present invention in determining antibody A glycolsylation, N-terminal pyroglutamic acid cyclization and C-terminal de-lysination were evaluated. Chromatography and mass spectrometry conditions were the same as described in Example 1.1. Data processing procedure was the same as described in Example 1.2.

Five continuous measurements were made, and the results were shown in Table 2. The measured results of the proportion of each IgG1 glycoform, and the proportions of N-terminal pyroglutamic acid cyclization and C-terminal de-lysination modification have a RSD % of less than 0.5%, the results of the contents of the glycoforms have a RSD % of less than 7%.

Five parallel processing samples were measured, and the results are shown in Table 3. The measured results of the proportions of N-terminal pyroglutamic acid cyclization and C-terminal de-lysination modification have a RSD % of less than 1%, the results of the contents of the glycoforms have a RSD % of less than 7%.

TABLE 2

Method Accuracy Measurement

| Terminal modification or glycoforms | Percentage (%) | | | | | | RSD (%) |
|---|---|---|---|---|---|---|---|
| | 1 | 2 | 3 | 4 | 5 | Average | |
| Light chain glutamic acid | 83.51 | 83.55 | 83.49 | 83.59 | 83.58 | 83.54 | 0.05 |
| G0F heavy chain glutamic acid | 90.10 | 89.58 | 90.04 | 90.04 | 89.81 | 89.91 | 0.24 |
| G0F heavy chain de-lysine | 87.95 | 88.17 | 88.15 | 88.43 | 87.99 | 88.14 | 0.22 |
| G0F | 74.40 | 74.03 | 73.22 | 73.80 | 74.25 | 73.94 | 0.62 |
| G1F | 12.64 | 12.79 | 12.76 | 13.01 | 13.13 | 12.87 | 1.55 |
| Man5 | 4.61 | 4.75 | 5.34 | 5.10 | 4.79 | 4.92 | 6.09 |
| G0F-GN | 4.10 | 4.15 | 4.40 | 3.98 | 3.85 | 4.10 | 5.02 |
| G0 | 4.24 | 4.28 | 4.27 | 4.12 | 3.98 | 4.18 | 3.06 |

TABLE 3

Method Reproducibility Measurement

| Terminal modification or glycoforms | Percentage (%) | | | | | | RSD (%) |
|---|---|---|---|---|---|---|---|
| | 1 | 2 | 3 | 4 | 5 | Average | |
| Light chain glutamic acid | 83.51 | 83.55 | 83.49 | 83.59 | 83.58 | 83.54 | 0.05 |
| G0F heavy chain glutamic acid | 90.10 | 89.58 | 90.04 | 90.04 | 89.81 | 89.91 | 0.24 |
| G0F heavy chain de-lysine | 87.95 | 88.17 | 88.15 | 88.43 | 87.99 | 88.14 | 0.22 |
| G0F | 74.40 | 73.92 | 74.57 | 74.03 | 73.40 | 74.06 | 0.62 |
| G1F | 12.64 | 13.16 | 12.69 | 13.21 | 13.21 | 12.98 | 2.24 |
| Man5 | 4.61 | 4.80 | 4.72 | 4.73 | 4.86 | 4.74 | 1.98 |
| G0F-GN | 4.10 | 3.87 | 4.06 | 4.09 | 4.07 | 4.04 | 2.36 |
| G0 | 4.24 | 4.24 | 3.96 | 3.94 | 4.46 | 4.17 | 5.24 |

In summary, the accuracy and reproducibility of the method are good.

1.4 Optimization of the Mobile Phase

The impact of mobile phase elution gradients on the chromatographic separation of the light and heavy chains was evaluated based on reversed-phase ultrahigh pressure liquid chromatography. To prepare the sample, 5 μg antibody A was added to 10 μL 6 M guanidine hydrochloride solution, followed by the addition of 0.5 M DTT solution 2 μL and finally an appropriate amount of 6 M guanidine hydrochloride solution, to make a final DTT concentration of 50 mM; reacting for 45 min at 65° C. The reaction products were separated with different mobile phase gradients, and other chromatographic and mass spectrum conditions were the same as Example 1.1. The mobile phase X was 0.1% formic acid in water, mobile phase Y was 0.1% formic acid in acetonitrile, and the flow rate was 0.4 mL/min. Four elution gradients were investigated, as follows:

Gradient 1: 0-5 min, 10% Y; 5-5.1 min, 10%-18% Y; 5.1-15 min, 18%-28% Y; 15-15.1 min, 28%-90% Y; 15.1-19.0 min, 90% Y; 19.0-19.1 min, 90%-10% Y; 19.1-22.0 min, 10% Y.

Gradient 2: 0-5 min, 10% Y; 5-5.1 min, 10%-25% Y; 5.1-8 min, 25%-27% Y; 8-18 min, 27%-30% Y; 18-18.1 min, 30%-90% Y; 18.1-21.0 min, 90% Y; 21.0-21.1 min, 90%-10% Y; 21.1-24.0 min, 10% Y.

Gradient 3: 0-5 min, 10% Y; 5-5.1 min, 10%-25% Y; 5.1-8 min, 25%-26% Y; 8-18 min, 26%-28% Y; 18-18.1 min, 28%-90% Y; 18.1-21.0 min, 90% Y; 21.0-21.1 min, 90%-10% Y; 21.1-24.0 min, 10% Y.

Gradient 4: 0-5 min, 10% Y; 5-5.1 min, 10%-25% Y; 5.1-6 min, 25%-26% Y; 6-10 min, 26%-27% Y; 10-15 min, 27%-32% Y; 15-15.1 min, 32%-90% Y; 15.1-18.0 min, 90% Y; 18-18.1 min, 90%-10% Y; 18.1-21.0 min, 10% Y.

Figures 2, 2A, 3:
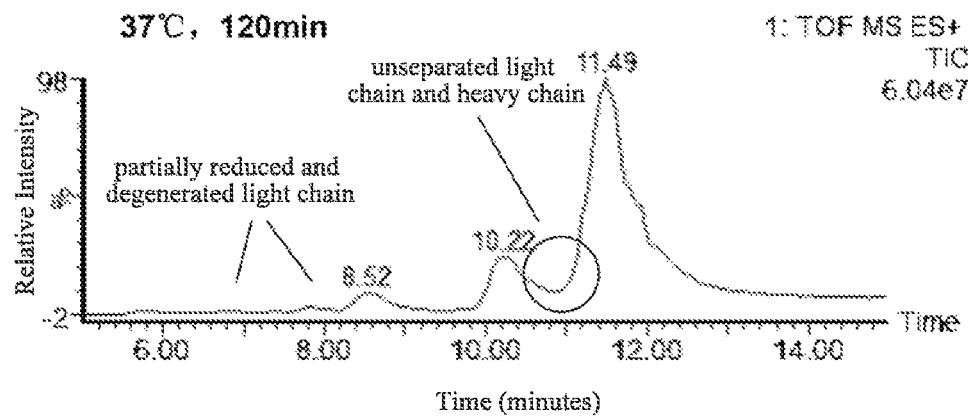
Figures 1, 2B:
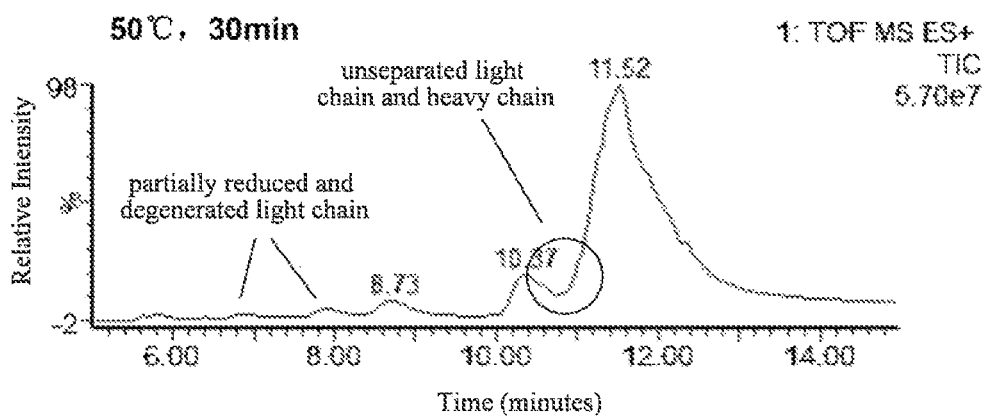
Figures 2, 2B:
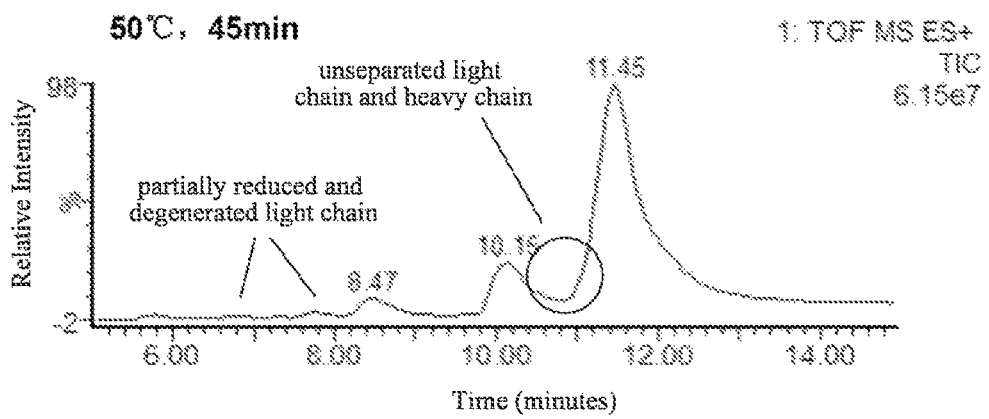
Figures 2, 2B, 3:
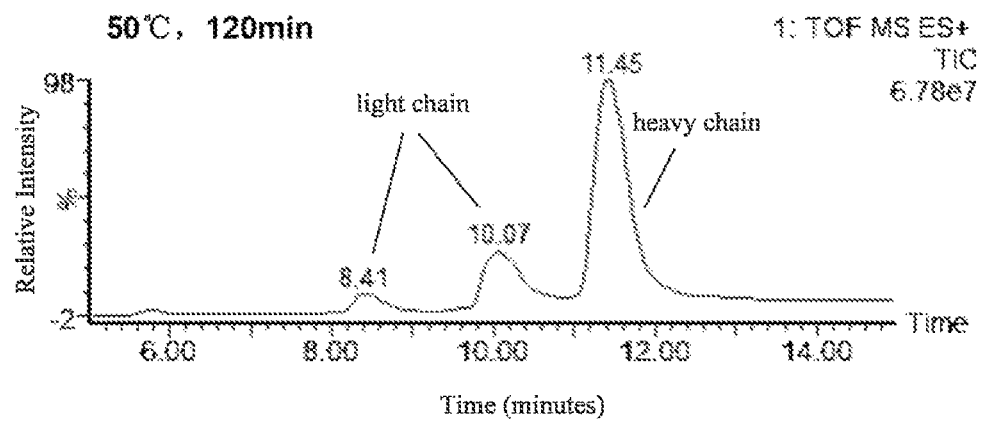
Figures 1, 2C:
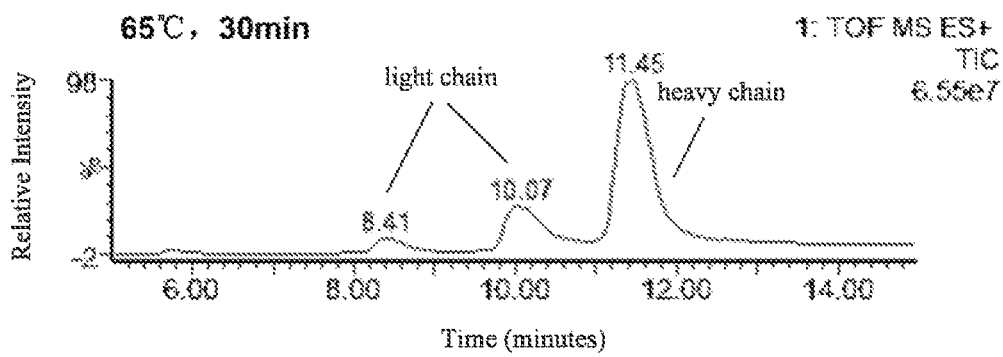
Figures 2, 2C:
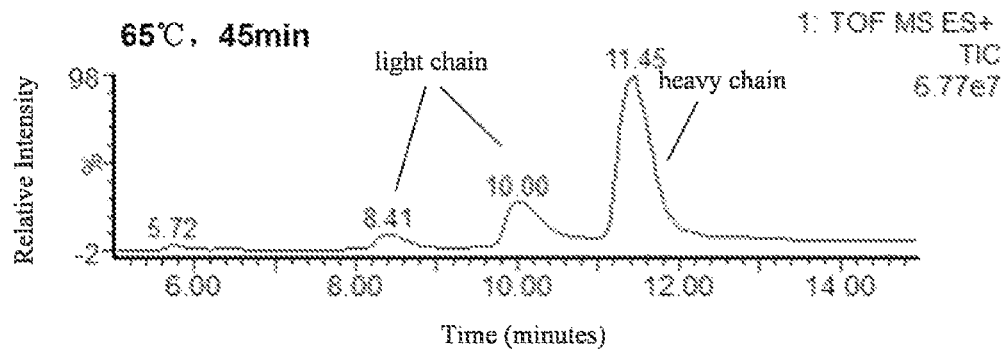
Figures 2, 2C, 3:
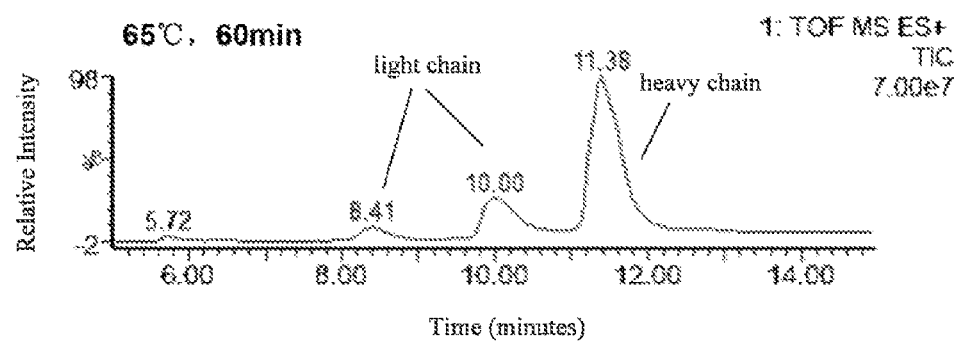
Figure 3A:
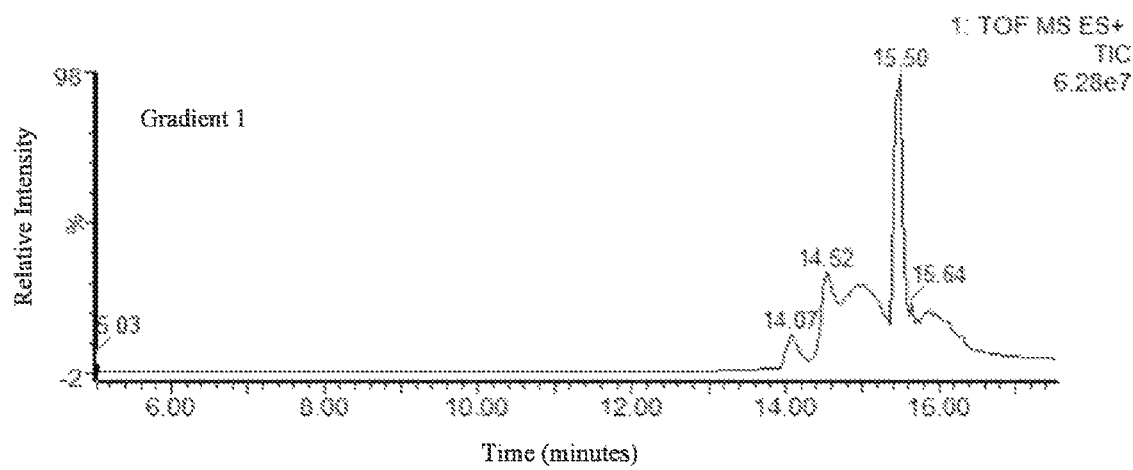
Figure 3B:
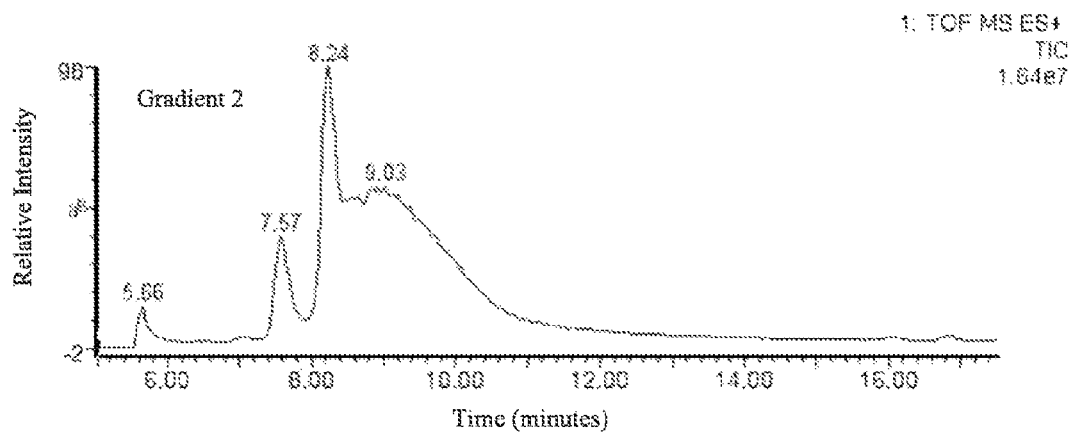
Figure 4A:
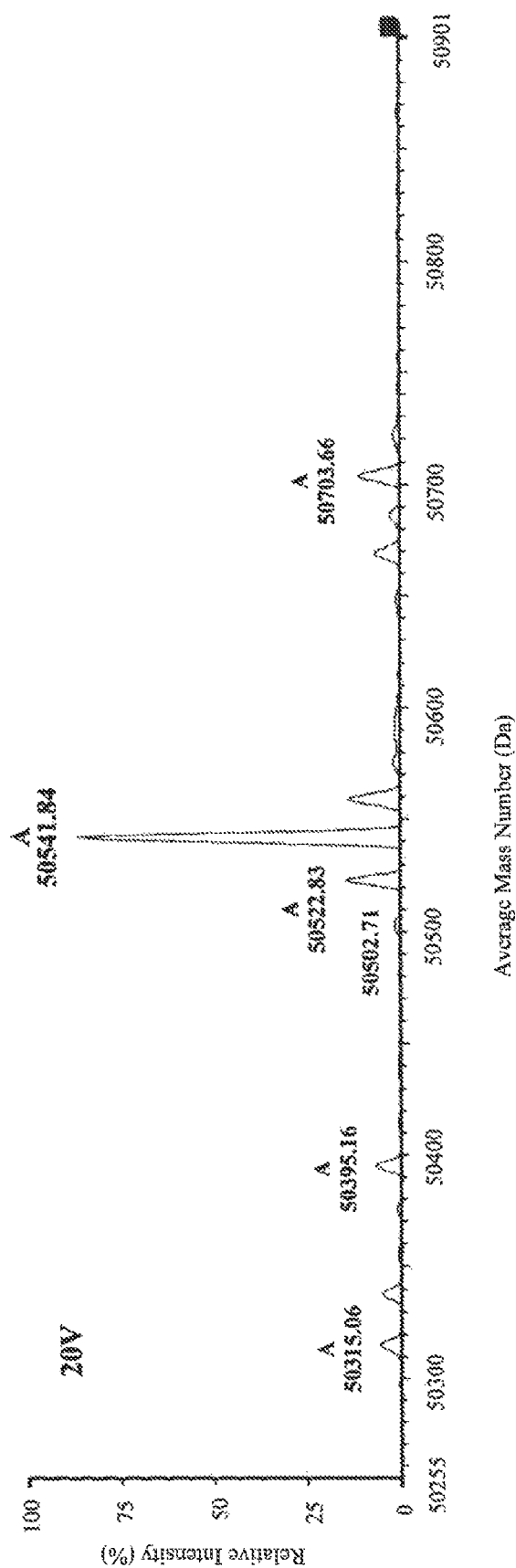
FIGS. 4A-4D show the effects of different cone voltages (20V, 25V, 30V, and 40V) on deconvoluted molecular weight of the heavy chain MS peak intensities in Example 1.
Figure 4B:
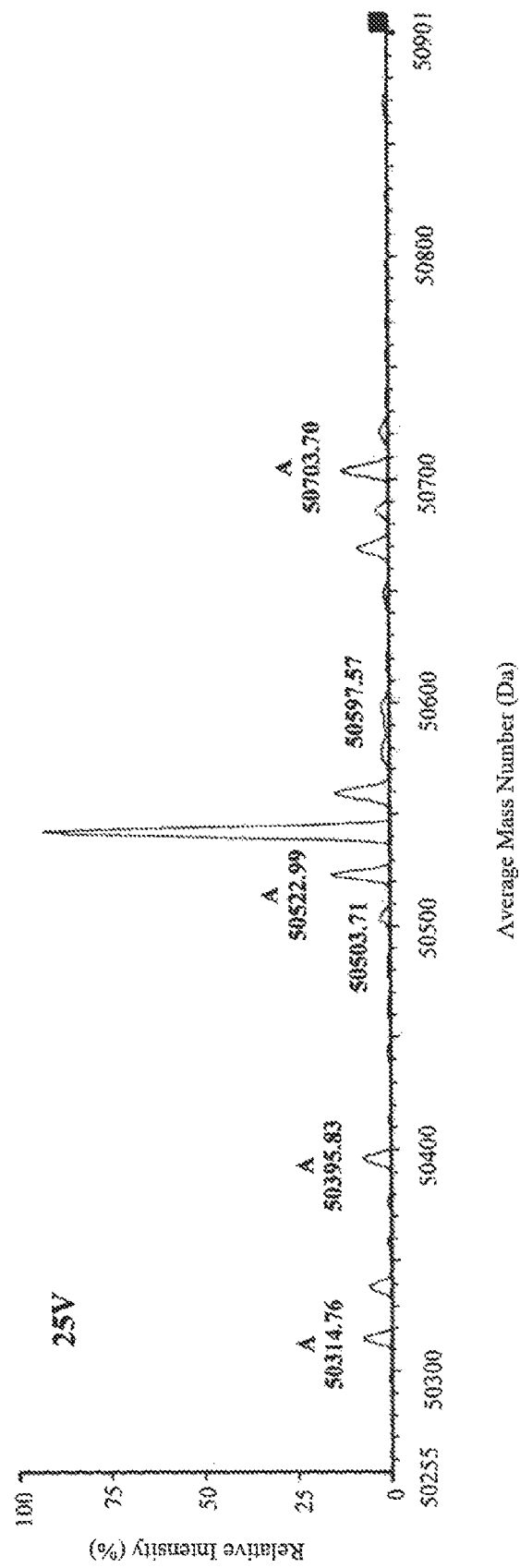
Figure 4C:
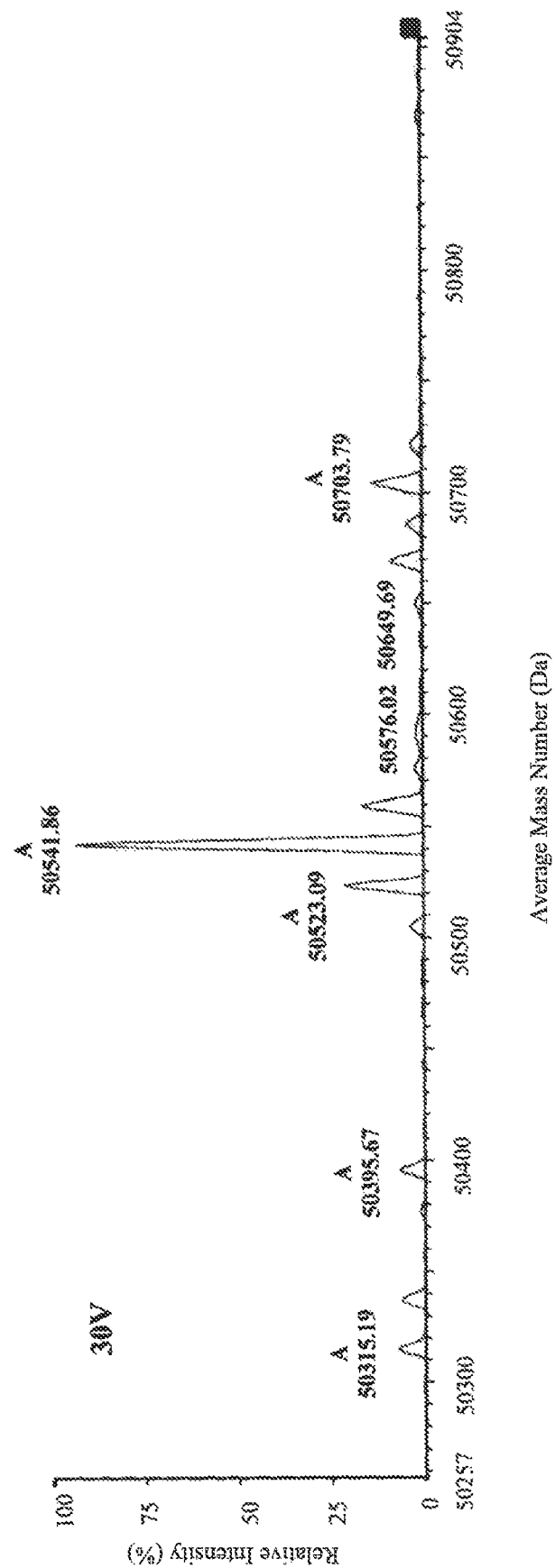
Figure 4D:
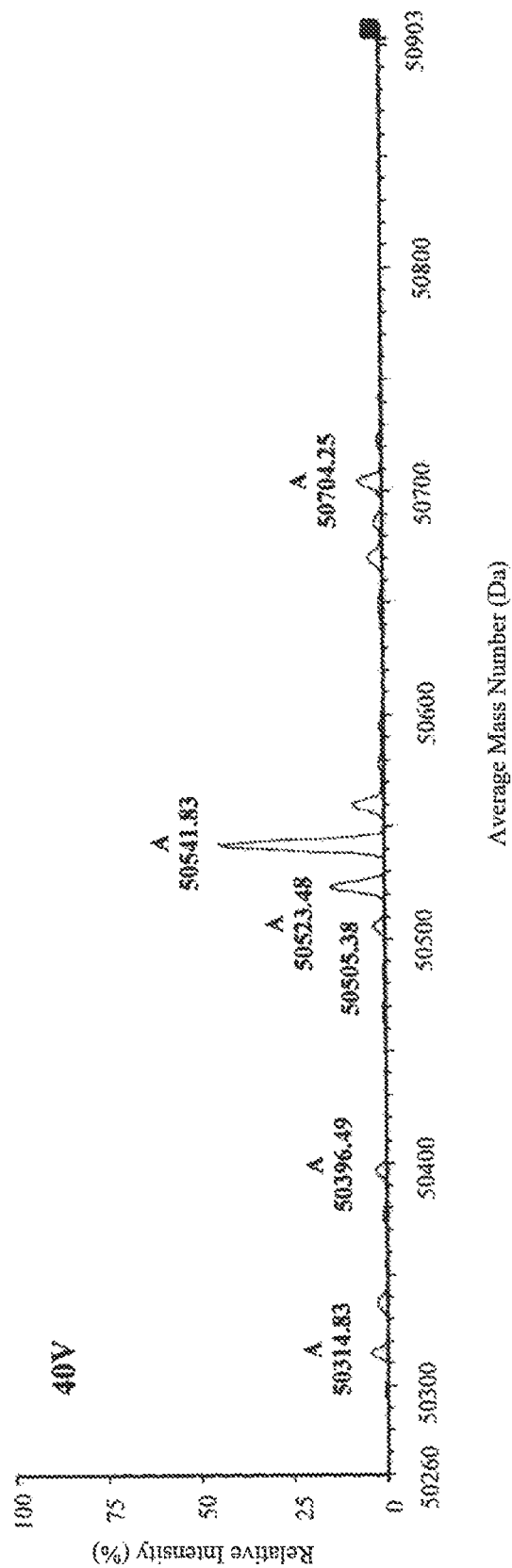

The chromatographic separation of light chain and heavy chains were shown in FIG. 3. In summary, the optimal mobile phase elution gradient to baseline separate light and heavy chains was gradient 4: 0-5 min, 10% Y; 5-5.1 min, 10%-25% Y; 5.1-6 min, 25%-26% Y; 6-10 min, 26%-27% Y; 10-15 min, 27%-32% Y; 15-15.1 min, 32%-90% Y; 15.1-18.0 min, 90% Y; 18.0-18.1 min, 90%-10% Y, 18.1-21.0 min, 10% Y.

1.5 Optimization of Mass Spectrum Conditions

Based on the optimized mobile phase elution gradient (0-5 min, 10% Y; 5-5.1 min, 10%-25% Y; 5.1-6 min, 25%-26% Y; 6-10 min, 26%-27% Y; 10-15 min, 27%-32% Y; 15-15.1 min, 32%-90% Y; 15.1-18.0 min 90% Y: 18.0-18.1 min 90%-10% Y; 18.1-21.0 min 10% Y), the impacts of mass spectrum parameters on light and heavy chains MS signals after baseline separation were investigated. Cone gas flow, desolvation gas and desolvation temperature had little effects on MS signals, and generally use the parameters recommended by equipment suppliers. The method of the present invention optimized sampling cone voltage. To prepare the sample, 5 μg antibody A was added to 10 μL 6 M guanidine hydrochloride solution, followed by the addition of 0.5 M DTT solution 41 and finally an appropriate amount of 6 M guanidine hydrochloride solution, to make a final DTT concentration of 50 mM; reacting for 45 min at 65° C. The reaction products were separated under the chromatographic conditions of Example 1.1, and the mass spectrometry sampling cone voltage was set to 20V, 25V, 30V, and 40V and other mass spectrum conditions were the same as Example 1.1. As the voltage increases, the total ion flow (peak area) of the light and heavy chains has increased. As shown in FIG. 4A to FIG. 4D, the deconvolved molecular weight mass spectrum signal of the heavy chain significantly increased between 20-25V, had no significant difference between 25-30V, but significantly decreased at 40V. In summary, the mass spectrometry sampling cone voltage of the method of present invention was determined as 25-30V.

EXAMPLE 2

Figure 5A:
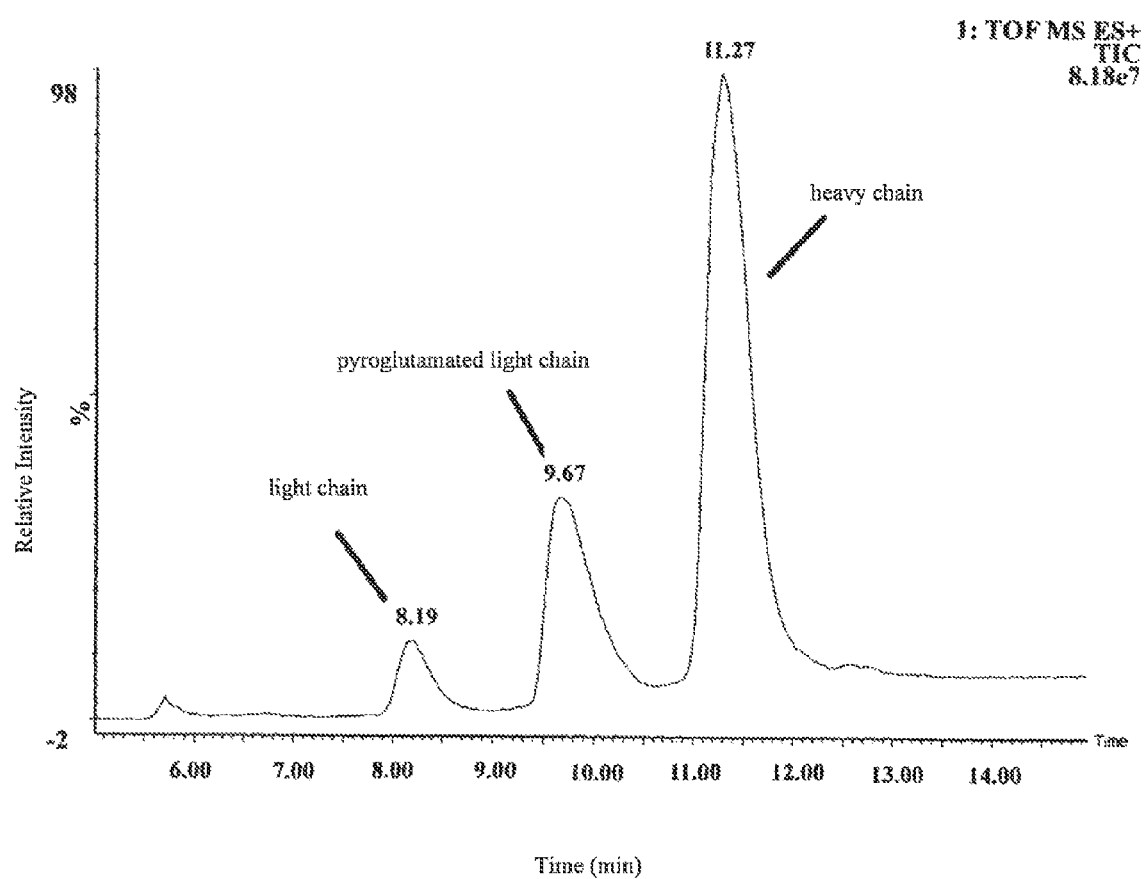
FIG. 5A shows chromatogram of antibody A determined after reduction in Example 2.
Figures 1, 5B:
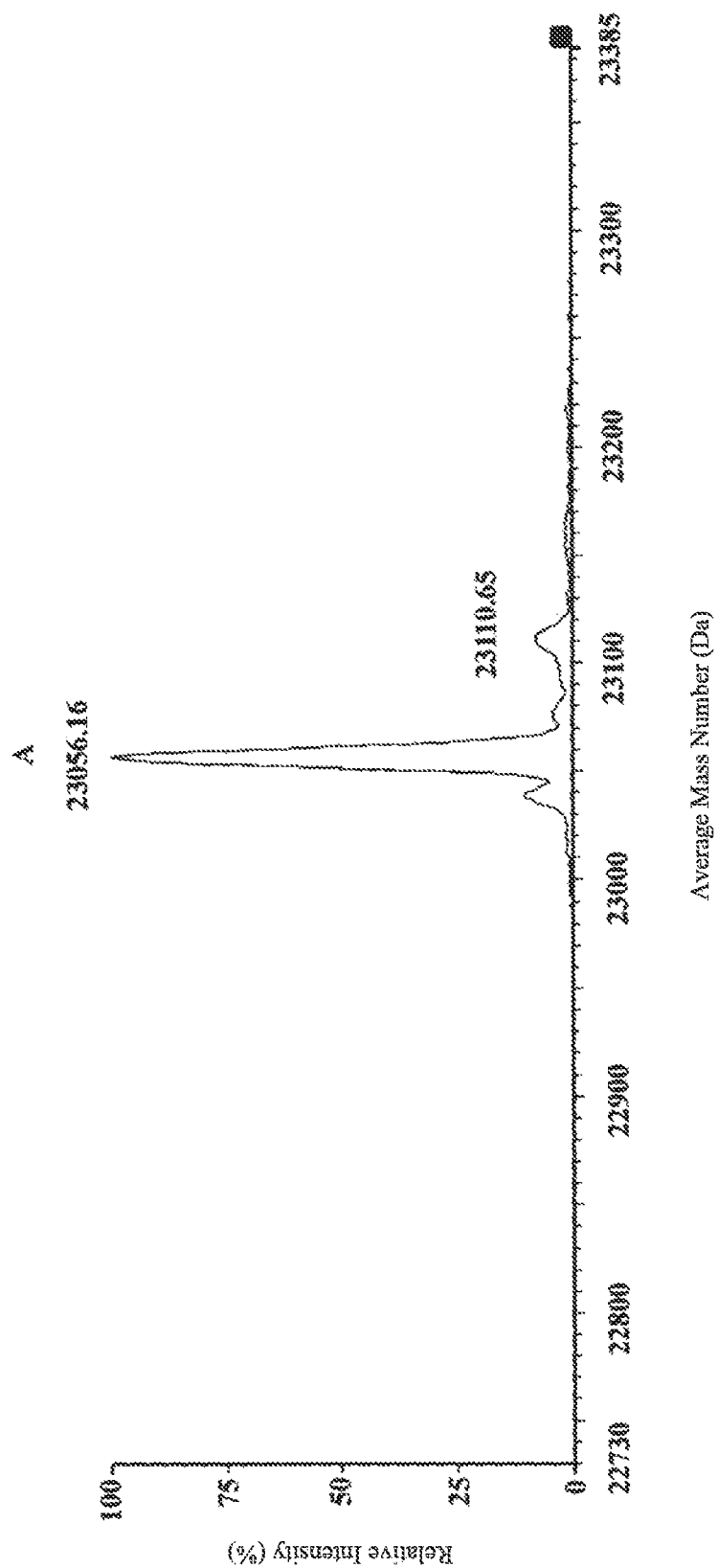
Figures 2, 5B:
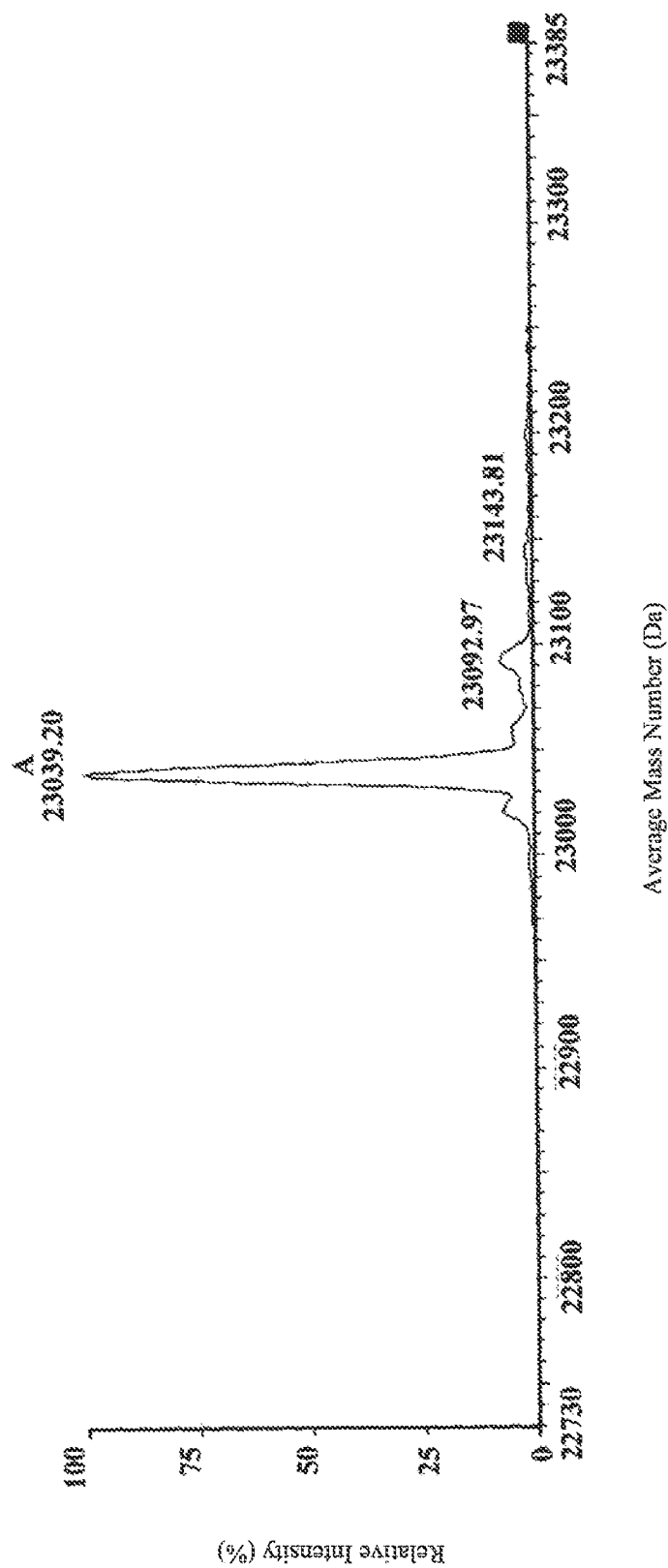
Figures 3, 5B:
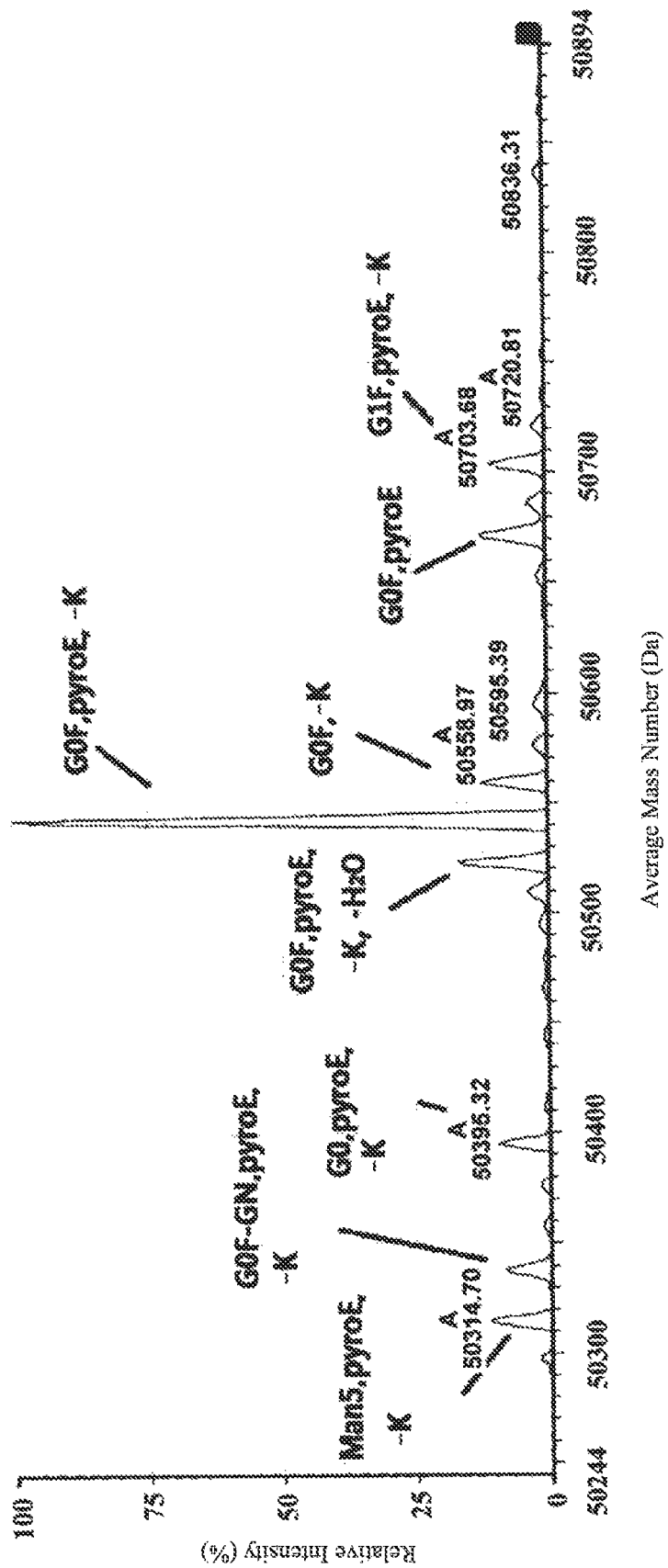
Figure 5C:
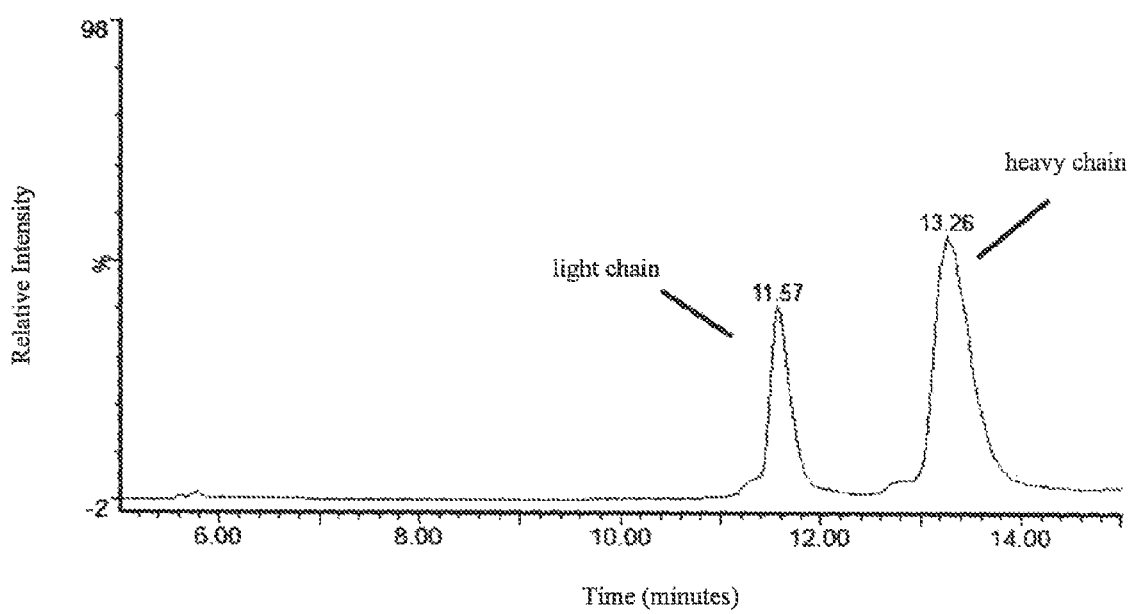
FIG. 5C shows chromatogram of antibody B determined after reduction in Example 2.
Figures 1, 5D:
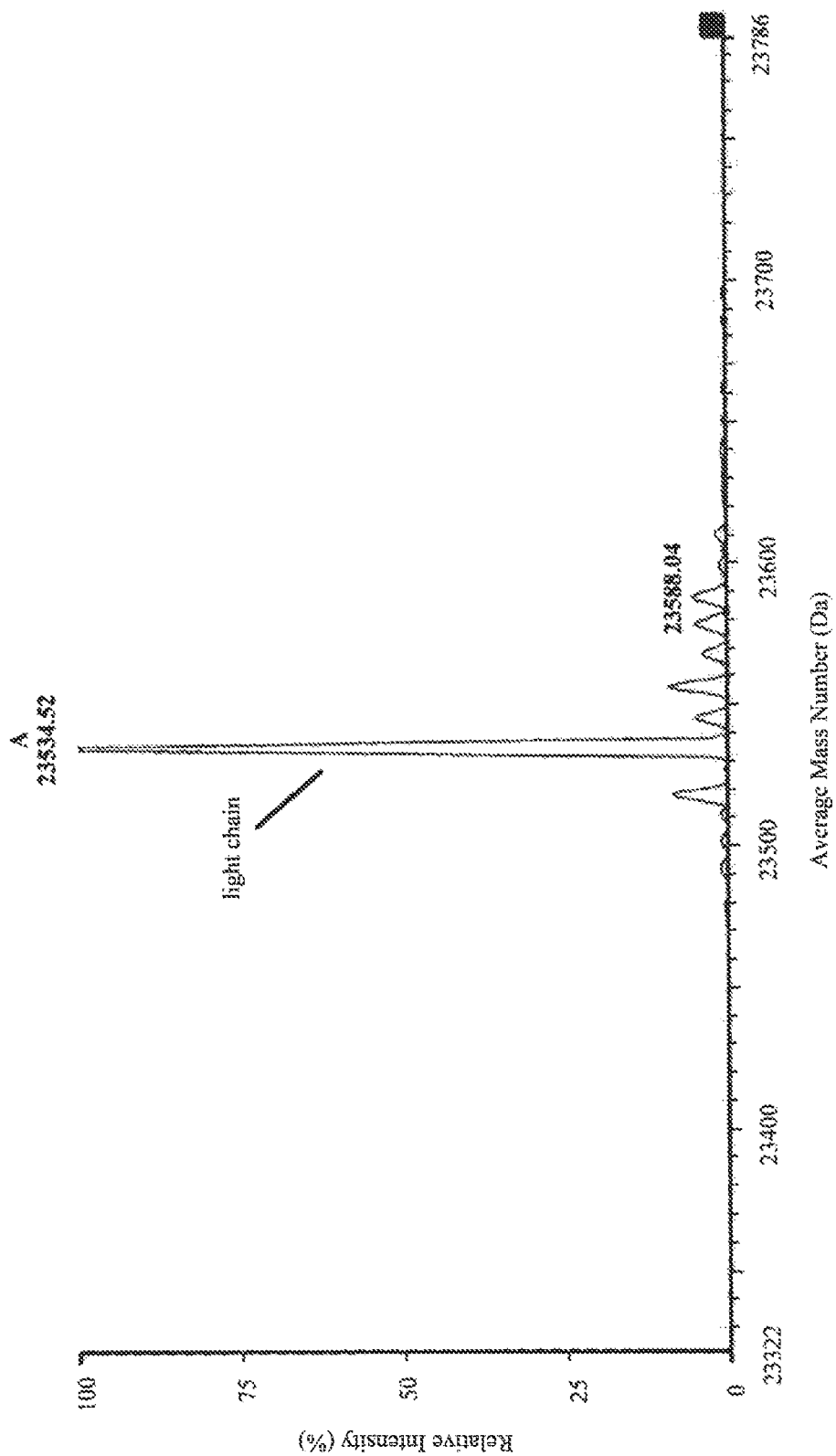
Figures 2, 5D:
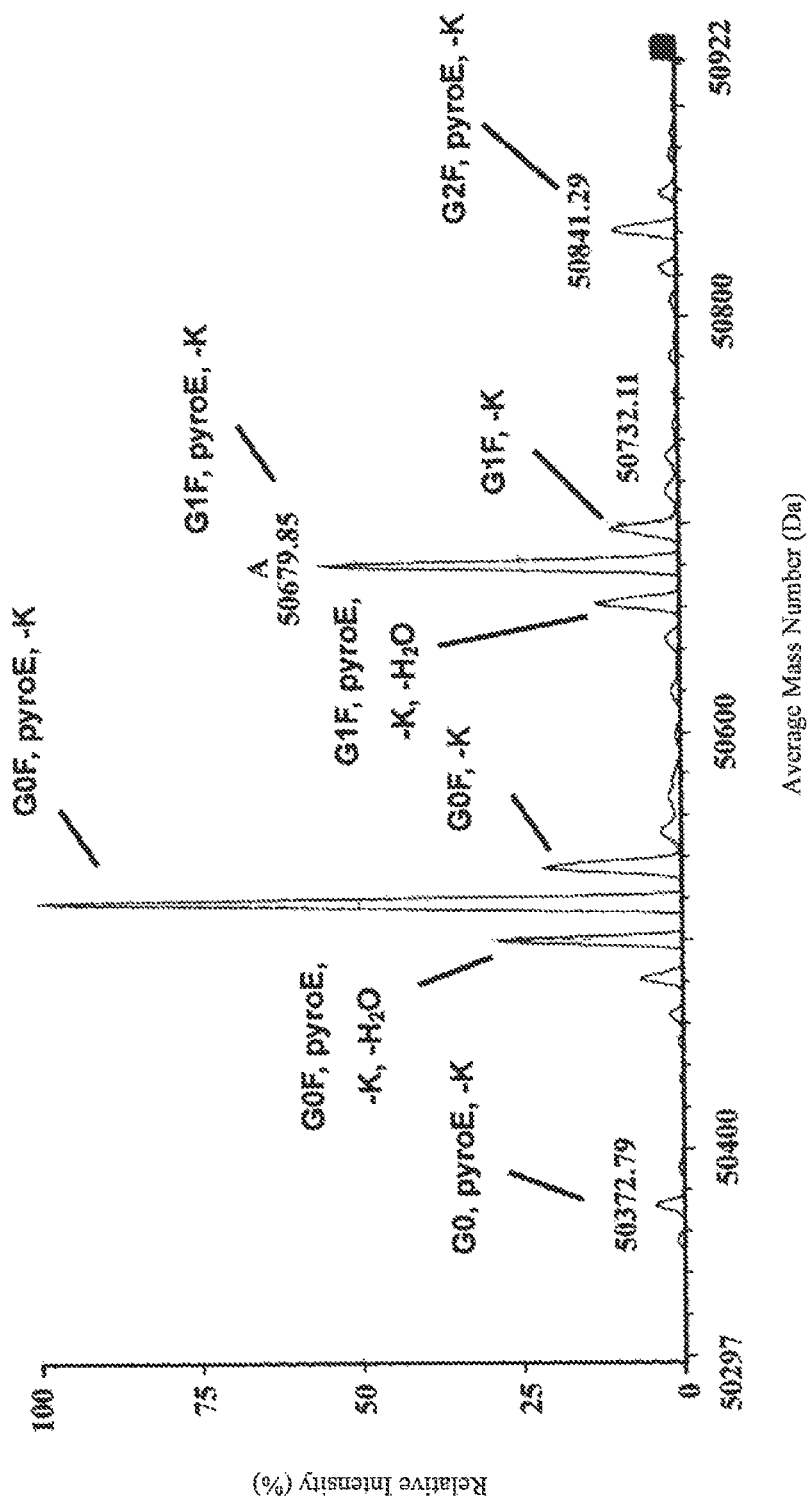

Determining the Glycosylation and Terminal Modification of Antibody A and Antibody B (IgG1) Using UPLC-MS Method of the Present Invention The glycosylation and terminal modification of antibody A and antibody B were analyzed using the optimized reduction conditions (5 μg antibody A was added to 10 μL 6 M guanidine hydrochloride solution, followed by the addition of 2 μL 0.5 M DTT solution and finally an appropriate amount of 6 M guanidine hydrochloride solution, to make a final DTT concentration of 50 mM; reacted for 45 min at 65° C.), UPLC separation (the same as Example 1.1), ESI-MS detection (the same as Example 1.1), and normalized data processing (the same as Example 1.2). The first amino acids at N-terminal of light chain and heavy chains of antibody A were both glutamine (Gln), for which pyroglutamic acid cyclization occurs readily. The first amino acids at N-terminal of light chain antibody B was glutamic acid (Glu), for which pyroglutamic acid cyclization does not occur readily, but the heavy chain has glutamine, for which pyroglutamic acid cyclization occurs readily. FIG. 5A is a chromatogram of antibody A after reduction measured by the UPLC-MS method of the present invention. FIG. 5B is the measured MS spectrum of the antibody, wherein FIG. 5B-1 is deconvolved MS spectrum of the chromatographic peak in FIG. 5A with a retention time of 8.19 min, i.e., unmodified light chain (LC), having a molecular weight of 23056 Da. FIG. 5B-2 is deconvolved MS spectrum of the chromatographic peak-N-terminal pyroglutaminated light chain in FIG. 5A with a retention time of 9.67 min, having a molecular weight of 23039 Da. FIG. 5B-3 is deconvolved MS spectrum of the peak in FIG. 5A with a retention time of 11.27 min, i.e., heavy chain (HC), and the MS peaks with different mass numbers in FIG. 5B-3 respectively represent the molecular weights of IgG1 with different glycoforms and terminal modification, and the measured and theoretical molecular weights thereof are shown in Table 4. The molecular weights of light and heave chains of antibody A measured by the method of present invention were highly consistent with theoretical values, at a high accuracy. Besides, the peaks with a mass number difference of 17 Da can be distinguished, for example, 50542 Da (G0F, pyroglutamic acid, de-lysine) and 50559 Da (G0F, de-lysine), indicating high resolution. FIG. 5C is a chromatogram of antibody B after reduction measured by the UPLC-MS method of the present invention. FIG. 5D is the measured MS spectrum of the antibody, wherein FIG. 5D-1 is deconvolved MS spectrum of the peak in FIG. 5C with a retention time of 11.57 min, i.e., light chain (LC), having a molecular weight of 23056 Da without pyroglutamination. FIG. 5D-2 is deconvolved MS spectrum of the peak in FIG. 5C with a retention time of 13.26 min, i.e., heavy chain (HC), and the MS peaks with different mass numbers in FIG. 5D-2 respectively represent the molecular weights of IgG1 with different glycoforms and terminal modification. As antibody A, the measured values and theoretical values of light and heavy chains of antibody B were highly consistent. By normalized calculation, the N-terminal pyroglutamination and C-terminal de-lysination of heavy chain of antibody B respectively were 70.6% and 97.8%, respectively; the contents of G0F, G1F, G2F, and G0 were 65.7%, 26.5%, 4.6%, and 3.2%, respectively.

TABLE 4

Theoretical molecular weights and measured molecular weights of heavy chain of antibody A with different types of glycoforms and terminal

| Glycosylation and terminal modification | Theoretical molecular weight | Actually measured molecular weight |
| --- | --- | --- |
| G0F, pyroglutamic acid, de-lysine | 50542 | 50542 |
| G0F, pyroglutamic acid, de-lysine, dehydrate | 50524 | 505023 |
| G0F, de-lysine | 50559 | 50559 |
| G0F, pyroglutamic acid | 50670 | 50670 |
| G1F, pyroglutamic acid, de-lysine | 50704 | 50704 |

TABLE 4-continued

Theoretical molecular weights and measured molecular weights of heavy chain of antibody A with different types of glycoforms and terminal

| Glycosylation and terminal modification | Theoretical molecular weight | Actually measured molecular weight |
| --- | --- | --- |
| Man5, pyroglutamic acid, de-lysine | 50314 | 50315 |
| G0F-GN, pyroglutamic acid, de-lysine | 50338 | 50339 |
| G0, pyroglutamic acid, de-lysine | 50395 | 50395 |

EXAMPLE 3

Determining the Glycosylation and Terminal Modification of Each Component of Antibody A after Purification Using UPLC-MS Method of the Present Invention In purification process of antibody A, a conventional strong cation-exchange chromatography was used, with 20 mM sodium phosphate buffer as loading buffer, 20 mM sodium phosphate and 1 M sodium chloride buffer (pH=6.0) as elution buffer, a flow rate of 200-400 cm/h. The eluting components were monitored by UV absorption at 280 nm. Then, the components of antibody A were collected in accordance with retention time: component 1 (4000-4300 min), component 2 (4300-4500 min), component 3 (4500-4650 min), component 4 (4650-4800 min), and component 5 (4800-5100 min). The glycosylation and terminal modifications of each component of the IgG1 were analyzed using the optimized reduction conditions (5 μg antibody A was added to 10 μL 6 M guanidine hydrochloride solution, followed by the addition of 2 μL 0.5 M DTT solution and finally an appropriate amount of 6 M guanidine hydrochloride solution, to make a final DTT concentration of 50 mM, reacting for 45 min at 65° C.), UPLC separation (the same as Example 1.1), ESI-MS detection (the same as Example 1.1), and normalized data processing (the same as Example 1.2). And the results are shown in Table 5, FIG. 6A-1 to FIG. 6A-2, and FIG. 6B-1 to FIG. 6B-2.

TABLE 5

Detected results of glycosylation and terminal modifications for each purified component collected by cation-exchange resin

| Terminal modifications or glycoforms | Percentage (%) | | | | |
| --- | --- | --- | --- | --- | --- |
| | 1 | 2 | 3 | 4 | 5 |
| Light chain glutamic acid | 95.36 | 75.88 | 57.89 | 59.14 | 48.16 |
| G0F heavy chain glutamic acid | 86.49 | 88.05 | 86.31 | 75.48 | 65.53 |
| G0F heavy chain de-lysine | 95.63 | 93.85 | 90.88 | 91.81 | 92.30 |
| G0F | 66.45 | 66.95 | 59.98 | 59.14 | 62.33 |
| G1F | 14.39 | 12.82 | 11.83 | 10.47 | 8.27 |
| Man5 | 5.53 | 7.24 | 10.55 | 11.61 | 9.16 |
| G0F-GN | 6.90 | 6.88 | 10.09 | 11.49 | 14.11 |
| G0 | 6.72 | 6.11 | 7.55 | 7.28 | 6.12 |

Figures 1, 6A:
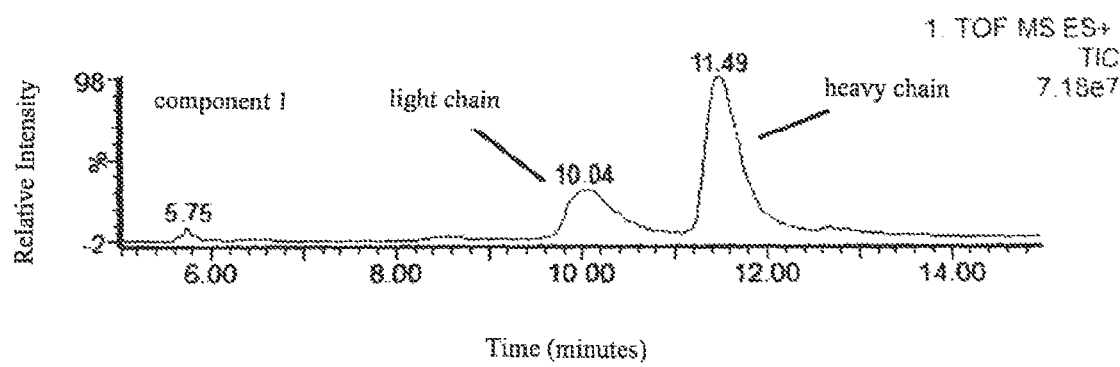
Figures 2, 6A:
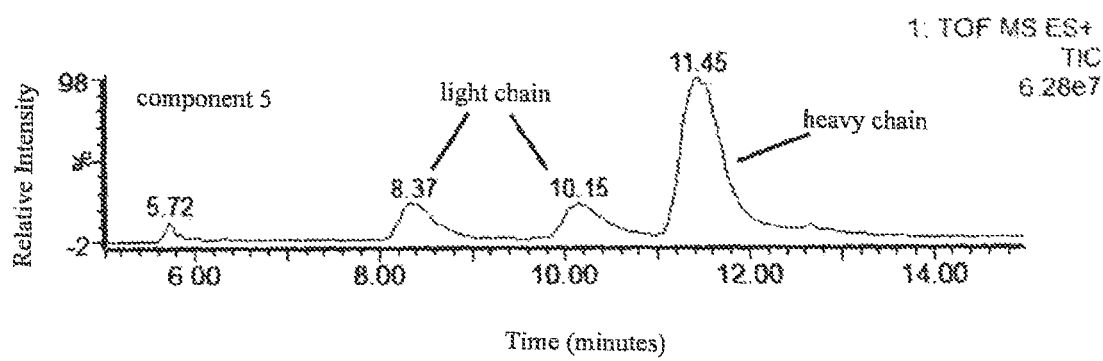
Figures 1, 6B:
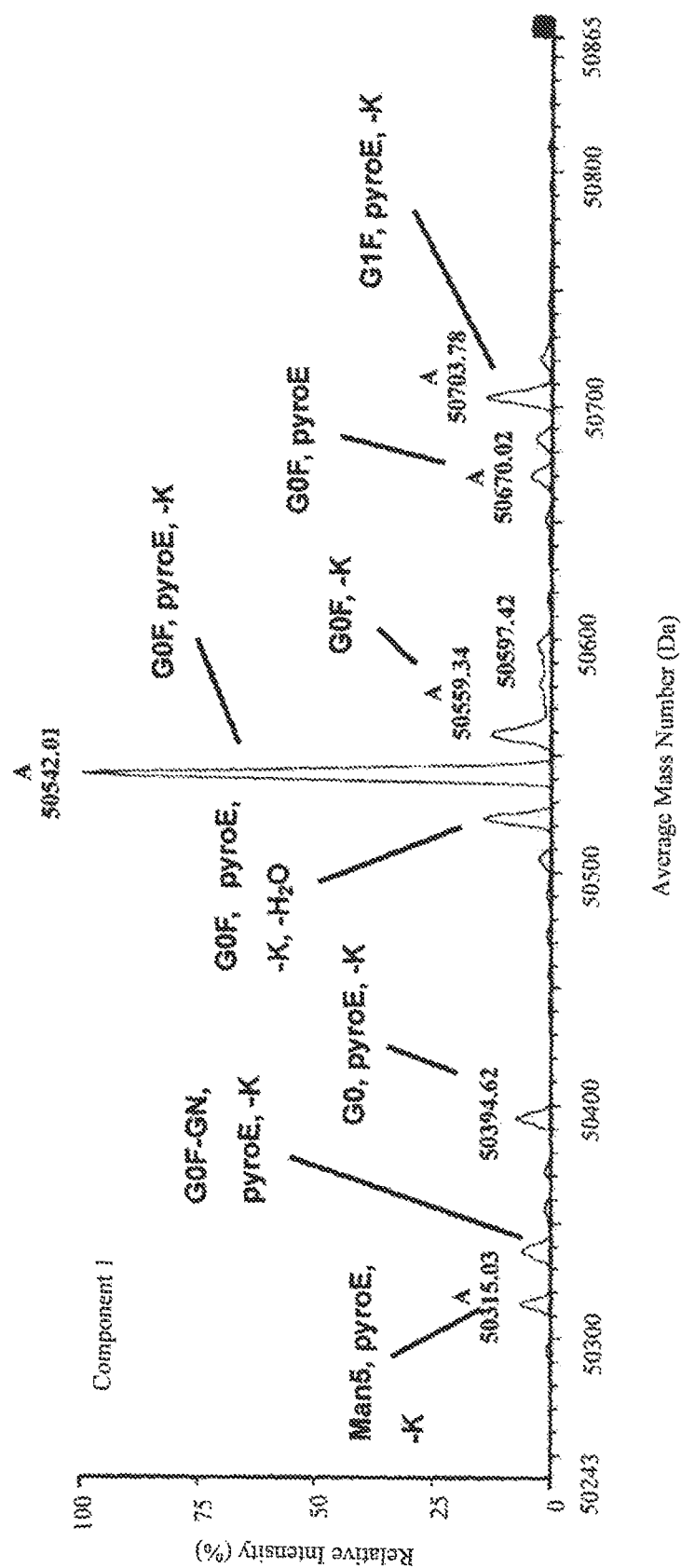
Figures 2, 6B:
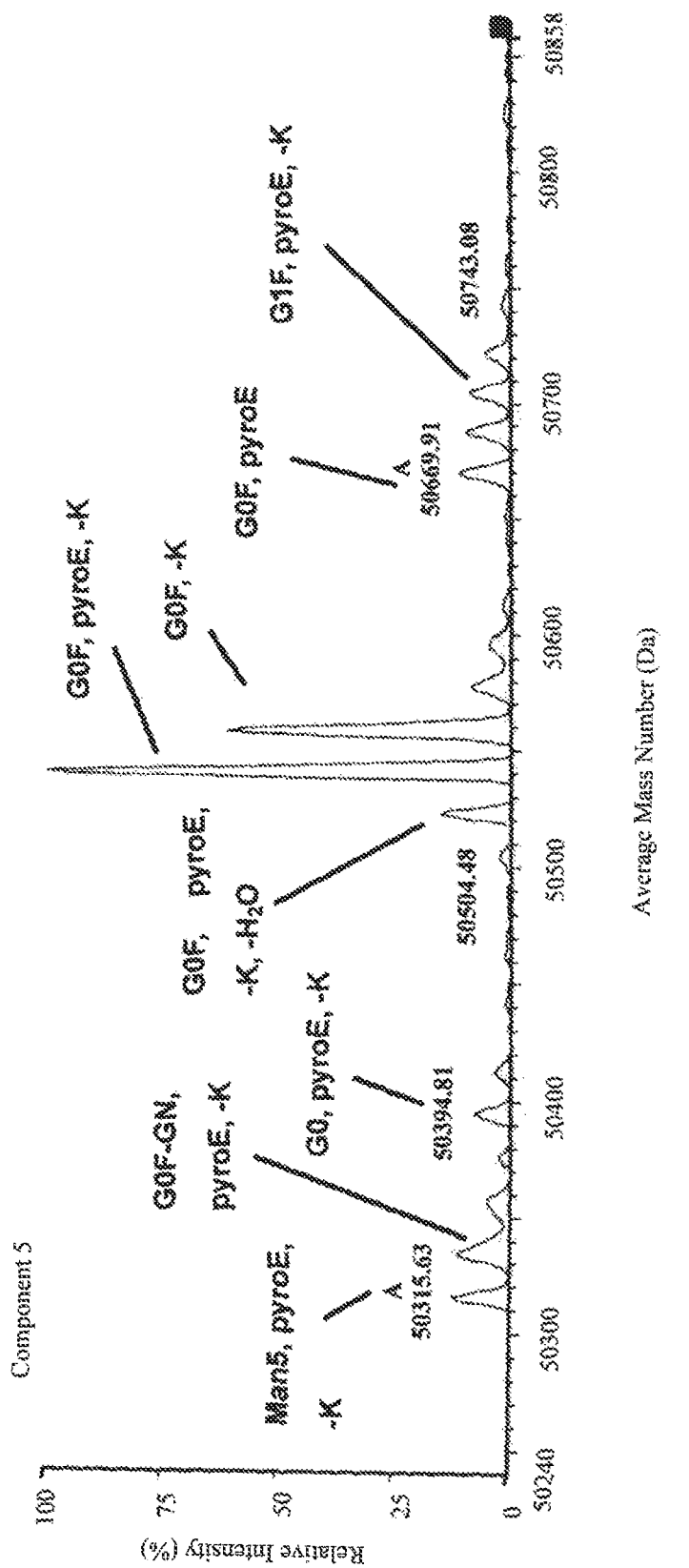

FIG. 6A-1 to FIG. 6A-2 were chromatograms of components 1 and 5 measured after reduction, and FIG. 6B-1 to FIG. 6B-2 were MS spectra of components 1 and 5 heavy chains.

The results showed that, from component 1 to component 5, N-terminal pyroglutamination of light chain (from 95.36% to 48.16%) and pyroglutamination of heavy chain (from 86.49% to 65.53%) gradually decreased; the glycosylated portions, G1F decreased from 14.39% (component 1) to 8.27% (component 5), and Man5 and G0F-GN increased from 5.53% to 9.16%, and from 6.72% to 14.11%, respectively. Therefore, the method of present invention can be applicable to monitor the difference in the glycosylation and terminal modifications of samples during antibody purification process.

EXAMPLE 4

Figure 7:
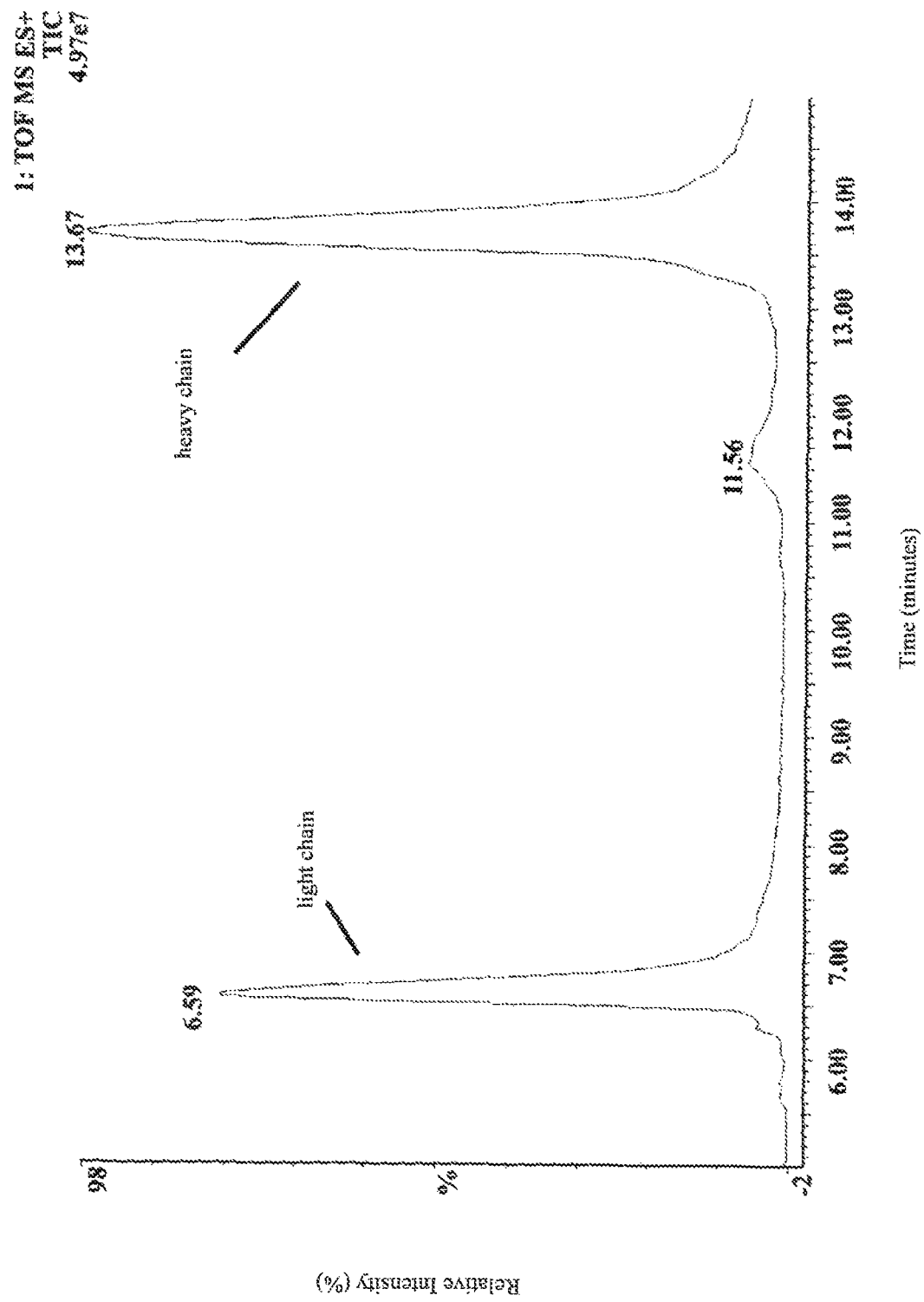
FIG. 7 shows chromatogram of antibody C (IgG2) determined after reduction in Example 4. pyroE is N-terminal pyroglutamic acid, —K means C-terminal de-lysine, and —H$_2$O means dehydrated.

Determining Glycosylation and Terminal Modifications of Each Component of Antibody C (IgG2) Using UPLC-MS Method of the Present Invention The glycosylation and terminal modifications of antibody C were analyzed using the optimized reduction conditions (5 μg antibody A was added to 10 μL 6 M guanidine hydrochloride solution, followed by the addition of 2 μL 0.5 M DTT solution and finally an appropriate amount of 6 M guanidine hydrochloride solution, to make a final DTT concentration of 50 mM; reacting for 45 min at 65° C.), UPLC separation (the same as Example 1.1), ESI-MS detection (the same as Example 1.1), and normalized data processing (the same as Example 1.2). FIG. 7 is a chromatogram of antibody C after reduction measured by the UPLC-MS method of the present invention, with the retention time of light chain (LC) being 6.6 min, and the retention time of heavy chain (HC) being 13.7 min. The first amino acids at N-terminal of light chain and heavy chain of antibody C were both glutamic acid (Glu), which does not tend to cyclize into pyroglutamic acid, and therefore pyroglutaminized light chain and heavy chain were not detected. Most heavy chains are subjected to C-terminal de-lysination. The glycoforms of antibody C mainly include G0F, G1F, Man5, G0, and G2F, and the molecular weights of corresponding de-lysinated heavy chains were 50206 Da, 50367 Da, 49978 Da, 50059 Da, and 50531 Da, consistent with the theoretical values; and the contents thereof were 58.0%, 19.5%, 13.7%, 6.6%, and 2.2%, respectively. Therefore, the method of the present invention is also applicable to the determination of glycosylation and terminal modifications of immunoglobulin IgG2.

EXAMPLE 5

The Kit Method of the Present Invention to Determine Glycosylation and Terminal Modifications of Antibody A The kit was consisted of reagent A and reagent B, wherein the reagent A was 6 M guanidine hydrochloride solution; and reagent B was 0.5 M DTT solution.

The method of using the kit to determine glycosylation and terminal modifications of antibody A specifically comprises:

20 μg antibody A (the protein concentration should be greater than 1 μg/μL, and a ultrafiltration centrifuge tube with a cut-off molecular weight of 10 kDa can be used to concentrate if the concentration was less than 1 μg/μL) was add to a certain amount of regent A to a final solution volume of 36 μL, followed by adding 4 μL reagent B, reacting for 45 min at 65° C. The reaction products were separated by UPLC (the same as Example 1.1), detected by ESI-MS (the same as Example 1.1), and the data were nonnalizedly processed (the same as Example 1.2), to analyze the glycosylation and terminal modifications of antibody A. The experiments were repeated for 5 days in succession (the samples were reprepared and determined).

The results showed that the light chain and heavy chain of antibody A were effectively separated, and achieved a baseline separation on chromatogram. As shown in Table 6, determined for 5 days in succession, the relative standard deviations RSD % of the measured values for light chain N-terminal pyroglutamination, heavy chain N-terminal pyroglutamination and C-terminal de-lysination were less than 2%. The relative standard deviations RSD % of the measured values for glycochains G0F, G1F, and G0 were less than 5%, and for Man5 and G0F-GN, they were less than 10%. In conclusion, the method of the present invention can achieve a standardized operation with good reproducibility, and can be used to establish a kit method for determining immunoglobulin glycosylation and terminal modifications.

TABLE 6

The reproducibility for applying the present method in determining terminal modifications of antibody A

| Terminal modifications | Modification ratio (%) | | | | | | RSD (%) |
| --- | --- | --- | --- | --- | --- | --- | --- |
| | Day 1 | Day 2 | Day 3 | Day 4 | Day 5 | Average | |
| Light chain pyroglutamination | 86.20 | 84.80 | 84.34 | 83.48 | 84.93 | 84.75 | 1.17 |
| G0F heavy chain pyroglutamination | 89.95 | 87.48 | 89.87 | 89.66 | 90.48 | 89.49 | 1.30 |
| G0F heavy chain de-lysination | 89.08 | 92.69 | 89.97 | 90.48 | 93.01 | 91.05 | 1.69 |

The above description of specific embodiments of the present invention does not limit the present invention, various changes and modification may be made by one skilled in the art without departing from the spirit of the present invention, and shall fall within the scope of the appended claims of the invention.

The invention claimed is:
1. A method for determining sample glycosylation and terminal modifications during purification process of immunoglobulin, consisting of the following steps of:
  Step 1) separating immunoglobulin by using cation-exchange chromatography, and collecting different components in accordance to retention time;
  Step 2) denaturing the components of immunoglobulin obtained in step 1) with a denaturant, followed by reducing the components with a reducing agent, to separate light chain and heavy chain of the immunoglobulin;
  Step 3) separating the light chain and the heavy chain of immunoglobulin of step 2) by using C4 reverse phase ultrahigh pressure liquid chromatography having a mobile phase X of 0.1% formic acid in water and mobile phase Y of 0.1% formic acid in acetonitrile to achieve a baseline separation of the light and the heavy chains;
  Step 4) measuring molecular weights of the light chain and the heavy chain obtained in step 3) with a mass spectrometer; and

Step 5) analyzing chromatographic data obtained in step 3) and mass spectrometric data obtained in step 4) to determine glycosylation and terminal modifications of said immunoglobulin.

2. The method according to claim 1, wherein said step 1) comprises: using conventional strong cation-exchange chromatography column with 20 mM sodium phosphate buffer as loading buffer, 20 mM sodium phosphate and 1 M sodium chloride buffer of pH=6.0 as elution buffer, and monitoring eluting components by UV absorption at 280 nm.

3. The method according to claim 1, wherein said step 2) comprises: adding 10-30 μL of 1-6 M guanidine hydrochloride aqueous solution a denaturant to a certain amount of immunoglobulin to denature the immunoglobulin, and after homogenously mixing, adding 1-4 μL dithiothreitol (DTT) aqueous solution as a reducing agent to reduce the immunoglobulin, wherein a final concentration of DTT in a reaction solution is 25-100 mM, and a final concentration of immunoglobulin is 0.2-3 μg/μL.

4. The method according to claim 3, wherein in said step 2), the final DTT concentration is 50 mM.

5. The method according to claim 3, wherein in said step 2), a temperature for immunoglobulin denaturation and reduction is 50-65° C., and a reaction time is 45 min-120 min.

6. The method according to claim 5, wherein in said step 2), the temperature for immunoglobulin denaturation and reduction is 65° C., and the reaction time is 45 min.

7. The method according to claim 1, wherein said step 4) comprises determining the molecular weights of the light and heavy chain obtained in said step 3) using electrospray ionization mass spectrometry, wherein at 0-5 min, a flow path leads to waste, and at 5-16 min, the flow path leads to MS; and collecting mass spectrometry data in positive ion mode,
wherein MS conditions are set as follows:
cone gas flow is about 50.0 L/Hr, desolivation gas is about 800.0 L/Hr, desolvation temperature is about 500° C., cone voltage is 20-40V, scan range is about 400-2500 Da, and scan time is about 1 s.

8. The method according to claim 7, wherein the cone voltage is 25-30V.

9. The method according to claim 1, wherein said step 5) comprises calculating the proportion of N-terminal pyroglutamination of light chain of immunoglobulin from a chromatographic peak area obtained in step 3); and calculating relative contents of glycoforms and proportions of N-terminal pyroglutamination and C-terminal de-lysination of heavy chain of immunoglobulin from the mass spectrometric data obtained in step 4).

10. The method according to claim 1, wherein the immunoglobulin is human immunoglobulin.

11. The method according to claim 10, wherein the immunoglobulin is human immunoglobulin IgG1 and IgG2 subtypes.

12. The method according to claim 1, wherein the glycosylation and terminal modifications of the immunoglobulin include N-terminal pyroglutamination of light chain, and asparagine glycosylation, N-terminal pyroglutamination, and C-terminal de-lysination of heavy chain of the immunoglobulin.

* * * * *